(12) United States Patent
Watanabe et al.

(10) Patent No.: US 7,902,109 B2
(45) Date of Patent: Mar. 8, 2011

(54) ORGANOMETALLIC COMPOUND, CATALYST FOR POLYMERIZATION OF POLAR GROUP-CONTAINING NORBORNENE AND PROCESS FOR PRODUCING NORBORNENE POLYMER

(75) Inventors: Saisuke Watanabe, Minami-Ashigara (JP); Osamu Uchida, Minami-Ashigara (JP)

(73) Assignee: Fujifilm Corporation, Minato-Ku, Tokyo (JP)

( * ) Notice: Subject to any disclaimer, the term of this patent is extended or adjusted under 35 U.S.C. 154(b) by 576 days.

(21) Appl. No.: 11/913,215

(22) PCT Filed: Apr. 28, 2006

(86) PCT No.: PCT/JP2006/309354
§ 371 (c)(1), (2), (4) Date: Oct. 31, 2007

(87) PCT Pub. No.: WO2006/121058
PCT Pub. Date: Nov. 16, 2006

(65) Prior Publication Data
US 2009/0247729 A1    Oct. 1, 2009

(30) Foreign Application Priority Data

May 6, 2005  (JP) ................... 2005-135166
Aug. 24, 2005  (JP) ................... 2005-243356

(51) Int. Cl.
C08F 4/609  (2006.01)
C08F 4/70  (2006.01)
C08F 232/04  (2006.01)
B01J 31/14  (2006.01)
B01J 31/22  (2006.01)

(52) U.S. Cl. ......... 502/121; 502/103; 502/117; 502/152; 526/133; 526/160; 526/169.1; 526/171; 526/281

(58) Field of Classification Search .................. 502/152, 502/155, 103, 117, 121; 526/133, 134, 160, 526/169.1, 171, 308, 309, 943, 281
See application file for complete search history.

(56) References Cited

U.S. PATENT DOCUMENTS 4,659,843 A    4/1987 Binger et al.
6,825,307 B2   11/2004 Goodall

FOREIGN PATENT DOCUMENTS

| JP | 7-304834 A | 11/1995 |
|---|---|---|
| JP | 2006-052347 A | 2/2006 |
| WO | WO 00/20472 A1 | 4/2000 |
| WO | WO 2005/019277 A1 | 3/2005 |
| WO | WO 2005-054312 A1 | 6/2005 |

OTHER PUBLICATIONS

Form PCT/ISA/210 (International Search Report) dated Aug. 1, 2006.
Form PCT/ISA/237 (Written Opinion of the International Searching Authority) dated Aug. 1, 2005.
Kumiko Matsushita et al., "Polymerization of Norbornene and Derivatives Catalyzed by Ni and Pd Complexes", Nihon University, OM Chem-Tech Co., Ltd., IPA-019, Mar. 11, 2005, 3 pages, The 85th Spring Meeting Drafts of the Chemical Society of Japan, (cited in International Search Report, Written Opinion and on pp. 3-4 of the specification).
Joice P. Mathew et al., "($\eta^3$-Allyl)Palladium (II) and Palladium (II) Nitrile Catalysts for the Addition Polymerization of Norbornene Derivatives With Functional Groups", Macromolecules, 1996, vol. 29, pp. 2755-2763, American Chemical Society (cited on p. 2 of the specification).
B. S. Heinz et al., "Poly(Norbornene Carboxylic Acid Ester)S: Synthesis and Properties", Acta Polymer., 1997, vol. 48, pp. 385-391, VCH Verlagsgesellschaft mbH, Weinheim (cited on p. 2 of the specification).
Cecily Andes et al., "The Copolymerization of Functionalized Norbornenes and the Comparison of Reactivy Ratios Using Various Palladium Catalysts", Polymer Preprints, 2002, vol. 43, No. 2, pp. 963-964 (cited on pp. 2-3 of the specification).
Polymer Preprints, Japan, 2005, vol. 54, No. 1, p. 277, 1Pe037 (cited on pp. 4-5 of the specification).

*Primary Examiner* — Caixia Lu
(74) *Attorney, Agent, or Firm* — Buchanan Ingersoll & Rooney PC

(57) ABSTRACT

An organometallic compound obtained by mixing following (a), (b) and (c): (a) a neutral organopalladium complex that has a palladium atom and two organic ligands each having at least three carbon atoms participating in a bond to the palladium atom; (b) an organophosphorus compound having one phosphorus atom; and (c) a salt comprising: an anion having no unshared electron pair in a central atom; and a countercation. And a process for producing a norbornene compound polymer, the process comprising: subjecting at least one norbornene compound represented by formula (A) as defined in the specification to polymerization reaction in a presence of an organometallic complex catalyst produced by mixing compound (a) and compound (d) described in the specification.

8 Claims, No Drawings

ORGANOMETALLIC COMPOUND, CATALYST FOR POLYMERIZATION OF POLAR GROUP-CONTAINING NORBORNENE AND PROCESS FOR PRODUCING NORBORNENE POLYMER

TECHNICAL FIELD

The present invention relates to an organometallic compound, a catalyst for polymerization of a polar group-containing norbornene and a process for production of a polar group-containing norbornene polymer. Further, the present invention relates to a process for production of a polymer of a norbornene compound and, more particularly, it relates to a process for production of a polymer of a norbornene compound in the presence of an organometallic complex catalyst prepared from a neutral organopalladium complex.

BACKGROUND ART

Addition polymers of norbornene having a polar group in its side chain (hereinafter, referred to as a polar group-containing norbornene) are promising as optical films because they have high heat resistance and low double refraction and, further, hydrophilicity, water permeability and adhesion to other materials.

It has been known already that addition polymerization of polar group-containing norbornene is able to be achieved by the use of a cationic organopalladium complex having an organic ligand (allyl or methoxynorbornyl) where carbon atoms participating in the bonding are 3 (*Macromolecules*, 1996, volume 29, pages 2755 and *Acta Polymer,* 1997, volume 48, page 385). However, according to such a means, 1/50 to 1/550 equivalent of organopalladium complex is necessary to the polar group-containing norbornene and it is not industrially desirable in view of the manufacturing cost. In addition, the resulting polar group-containing norbornene polymer turns yellow and is not appropriate to be used as an optical film.

In the meanwhile, it has been known that a copolymerizing activity of triethoxysilylnorbornene/butylnorbornen is greatly improved when a cationic allyl palladium complex which is generated by addition of a salt containing a non-coordinate anion to a complex where bulky phosphine ligand and anionic ligand are coordinated to allyl palladium is used as a catalyst (U.S. Pat. No. 6,825,307 B2). However, in this complex, the yield in the polymerization reaction of ethyl norbornenecarboxylate and the yield in the polymerization of norbornene methyl acetate are as low as 0% and 1%, respectively (*Polymer Preprints,* 2002, volume 43, page 963) and, as such, there are some cases when no effective catalytic action takes place depending upon the type of the polar group-containing norbornene.

On the other hand, there is a description in Papers to be presented at the 85th Spring Meeting of the Chemical Society of Japan, 1PA-019 that a catalytic system where a salt comprising counter-cation and anion having no unshared electron pair in molecules is added to allylcyclopentadienyl palladium is effective for homopolymerization of norbornene. However, there is no description concerning polymerization of polar group-containing norbornene there.

As such, in the already-known catalytic system for addition polymerization of polar group-containing norbornene, there are problems such as that activity of the catalyst is low and that, in some types of polar group-containing norbornene, no polymerization proceeds.

Polymers having a norbornene compound as a main chain have high heat resistance, low double refraction and stability to moisture and, therefore, they are promising as optical films.

In a vinyl polymerization of such a norbornene compound, a production process using a transient metal complex as a catalyst has been particularly receiving public attention in recent years. For example, in Papers to be presented at the 85th Spring Meeting of the Chemical Society of Japan, 1PA-019 and Papers to be presented at the 54th Annual Meeting of the Polymer Society, 1Pe-037, it is mentioned that a catalytic system comprising allylcyclopentadienyl palladium and trityl tetrakis(pentafluorophenyl) borate is effective for homopolymerization of norbornene and for copolymerization of norbornene with methyl norbornenecarboxylate.

DISCLOSURE OF THE INVENTION

When the present inventor has applied the catalyst mentioned in the above-mentioned *Polymer Preprints,* 2002, volume 43, page 963 to polymerization of polar group-containing norbornene, no good polymer has been found to be produced. Accordingly, a first object of the present invention is to provide a catalytic system where a good catalytic activity is achieved in polymerization reaction of polar group-containing norbornene of a broad range.

Polymers of a norbornene compound prepared by using the catalyst mentioned in the above Papers to be presented at the 85th Spring Meeting of the Chemical Society of Japan, 1PA-019 and Papers to be presented at the 54th Annual Meeting of the Polymer Society, 1Pe-037 were found to turn yellow. When such polymers are used as a material for optical film, the film becomes yellowish and light transmission of the film lowers whereby they are not suitable as a material for films.

Under such circumstances, a second object of the present invention is to provide a process for production of polymers of a norbornene compound which are in small degree of coloration and able to be used as a material for films having high transparency. Further the second object is to provide a catalyst for producing such excellent polymers in a high yield and to provide a process for production of polymers of a norbornene compound using the same.

The present inventor has carried out intensive investigations for solving the above-mentioned first object and, as a result, it has been found that a catalyst produced by mixing of (a) a neutral organopalladium complex having palladium and two organic ligands where carbon atoms participating in bond to palladium are at least three, (b) an organophosphorus compound having one phosphorus atom and (c) a salt comprising anion having no unshared electron pair in central atom and a counter-cation has a high catalytic activity to polymerization reaction of polar group-containing norbornene of a broad range. As a result thereof, it is now possible to produce a polymer having no yellowish color. Further, the above-mentioned second object has been achieved by the following means.

Thus, the above-mentioned objects are able to be achieved by the following (1) to (16).

(1) An organometallic compound obtained by mixing following (a), (b) and (c):

(a) a neutral organopalladium complex that has a palladium atom and two organic ligands each having at least three carbon atoms participating in a bond to the palladium atom;

(b) an organophosphorus compound having one phosphorus atom; and (c) a salt comprising: an anion having no unshared electron pair in a central atom; and a counter-cation.

(2) The organometallic compound as described in (1) above,
wherein one organic ligand of the two organic ligands has three carbon atoms participating in a bond to the palladium atom, and the other organic ligand of the two organic ligands has five carbon atoms participating in a bond to the palladium atom.

(3) The organometallic compound as described in (2) above,
wherein the neutral organopalladium complex is represented by formula (I):

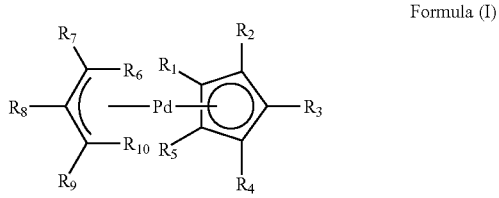

Formula (I)

wherein $R_1$, $R_2$, $R_3$, $R_4$, $R_5$, $R_6$, $R_7$, $R_8$, $R_9$ and $R_{10}$ each independently represents a hydrogen atom a halogen atom or a univalent organic group, and may be bonded each other to form a ring structure.

(4) The organometallic compound as described in (2) above,
wherein the neutral organopalladium complex is represented by formula (II):

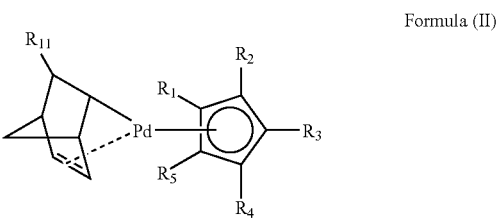

Formula (II)

wherein $R_1$, $R_2$, $R_3$, $R_4$, $R_5$ and $R_{11}$ each independently represents a hydrogen atom, a halogen atom or a univalent organic group, and may be bonded each other to form a ring structure; and
a dotted line represents a coordination bond.

(5) The organometallic compound as described in (2) above,
wherein the neutral organopalladium complex is represented by formula (III):

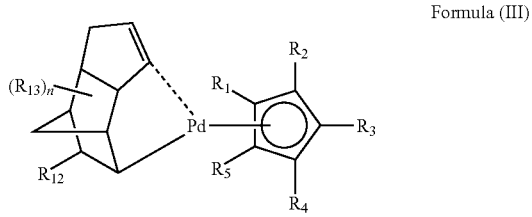

Formula (III)

wherein $R_1$, $R_2$, $R_3$, $R_4$, $R_5$, $R_{12}$ and $R_{13}$ each independently represents a hydrogen atom, a halogen atom or a univalent organic group, and may be bonded each other to form a ring structure;
n represents an integer of 1 to 12;
$(R_{13})_n$ represents substitutions of n number of $R_{13}$'s; and
a dotted line represents a coordination bond.

(6) The organometallic compound as described in (2) above,
wherein the neutral organopalladium complex is represented by formula (IV):

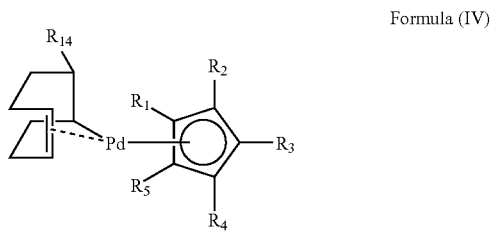

Formula (IV)

wherein $R_1$, $R_2$, $R_3$, $R_4$, $R_5$ and $R_{14}$ each independently represents a hydrogen atom, a halogen atom or a univalent organic group, and may be bonded each other to form a ring structure; and
a dotted line represents a coordination bond.

(7) A catalyst for polymerization of a polar group-containing norbornene, the catalyst is produced by utilizing an organometallic compound as described in any of (1) to (6) above.

(8) A process for producing a polar group-containing norbornene polymer, the process comprising:
polymerizing a polar group-containing norbornene by utilizing a catalyst for polymerization of a polar group-containing norbornene as described in (7) above.

(9) A process for producing a norbornene compound polymer, the process comprising:
subjecting at least one norbornene compound represented by formula (A) to polymerization reaction in a presence of an organometallic complex catalyst produced by mixing following compound (a) and compound (d):

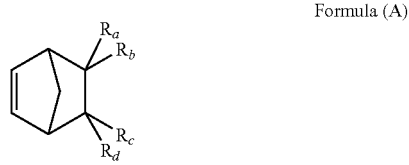

Formula (A)

wherein $R_a$, $R_b$, $R_c$ and $R_d$ each independently represents a hydrogen atom or a univalent organic group comprising a carbon atom and a hydrogen atom, and may be bonded each other to form a ring structure;
compound (a) is a neutral organopalladium complex that has a palladium atom and two organic ligands each having at least three carbon atoms participating in a bond to the palladium atom; and
compound (d) is a trisubstituted ammonium tetrakis(aryl) borate.

(10) A process for producing a norbornene compound polymer, the process comprising:
subjecting at least one norbornene compound represented by formula (A) and at least one norbornene compound represented by formula (B) to copolymerization reaction in a presence of an organometallic complex catalyst produced by mixing following compound (a) and compound (d):

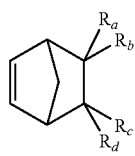

Formula (A)

wherein $R_a$, $R_b$, $R_c$ and $R_d$ each independently represents a hydrogen atom or a univalent organic group comprising a carbon atom and a hydrogen atom, and may be bonded each other to form a ring structure;

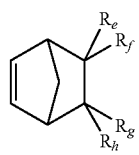

Formula (B)

wherein $R_e$, $R_f$, $R_g$ and $R_h$ each independently represents a hydrogen atom, a halogen atom or a univalent organic group, and may be bonded each other to form a ring structure, provided that at least one of $R_e$, $R_f$, $R_g$ and $R_h$ represents a univalent organic group and at least one of the univalent organic group(s) is a polar group;

compound (a) is a neutral organopalladium complex that has a palladium atom and two organic ligands each having at least three carbon atoms participating in a bond to the palladium atom; and compound (d) is a trisubstituted ammonium tetrakis(aryl) borate.

(11) The process for producing a norbornene compound polymer as described in (9) or (10) above,
wherein the trisubstituted ammonium is dialkylarylammonium.

(12) The process for producing a norbornene compound polymer as described in any of (9) to (11) above,
wherein one organic ligand of the two organic ligands has three carbon atoms participating in a bond to the palladium atom, and the other organic ligand of the two organic ligands has five carbon atoms participating in a bond to the palladium atom.

(13) The process for producing a norbornene compound polymer as described in (12) above,
wherein the neutral organopalladium complex is represented by formula (I):

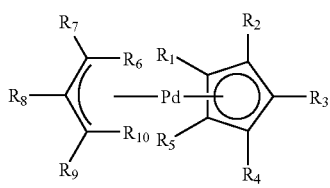

Formula (I)

wherein $R_1$, $R_2$, $R_3$, $R_4$, $R_5$, $R_6$, $R_7$, $R_8$, $R_9$ and $R_{10}$ each independently represents a hydrogen atom, a halogen atom or a univalent organic group, and may be bonded each other to form a ring structure.

(14) The process for producing a norbornene compound polymer as described in (12) above,
wherein the neutral organopalladium complex is represented by formula (II):

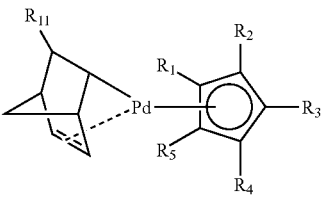

Formula (II)

wherein $R_1$, $R_2$, $R_3$, $R_4$, $R_5$ and $R_{11}$ each independently represents a hydrogen atom, a halogen atom or a univalent organic group, and may be bonded each other to form a ring structure; and a dotted line represents a coordination bond.

(15) The process for producing a norbornene compound polymer as described in (12) above,
wherein the neutral organopalladium complex is represented by formula (III):

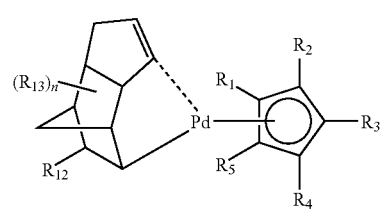

Formula (III)

wherein $R_1$, $R_2$, $R_3$, $R_4$, $R_5$, $R_{12}$ and $R_{13}$ each independently represents a hydrogen atom, a halogen atom or a univalent organic group, and may be bonded each other to form a ring structure; and n represents an integer of 1 to 12;

$(R_{13})_n$ represents substitutions of n number of $R_{13}$'s; and a dotted line represents a coordination bond.

(16) The process for producing a norbornene compound polymer as described in (12) above,
wherein the neutral organopalladium complex is represented by formula (IV):

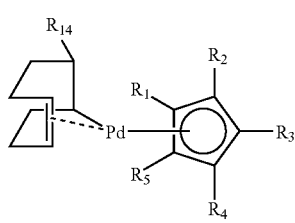

Formula (IV)

wherein $R_1$, $R_2$, $R_3$, $R_4$, $R_5$ and $R_{14}$ each independently represents a hydrogen atom, a halogen atom or a univalent organic group, and may be bonded each other to form a ring structure; and a dotted line represents a coordination bond.

BEST MODE FOR CARRYING OUT THE INVENTION

The present invention relating to the means for solving the first object will now be illustrated in detail as hereunder.

(Organometallic Compounds)

The organometallic compound of the present invention is prepared by mixing the following (a), (b) and (c).

(a) Neutral Organopalladium Complex

The neutral organopalladium complex used in the present invention is characterized in having palladium and two organic ligands where carbon atoms participating in the bond to palladium are at least three in each organic ligand and being neutral. Both of the two organic ligands are preferred to be univalent carboanions. Palladium is preferred to be a divalent palladium. When the two organic ligands are univalent carboanions and palladium is a divalent palladium, charge of the organopalladium complex as a whole is 0 which is neutral. The two organic ligands bond to palladium and carbon numbers participating in the bond are at least 3 for both.

Examples of the organic ligand where carbon numbers participating in the bond to palladium are 3 are $\eta^3$ allyl, bicycloheptenyl, cyclooctenyl, cyclooctatrienyl, hexahydromethanoindenyl and substituted ones thereof. Examples of the organic ligand where carbon numbers participating in the bond to palladium are 5 are $\eta^5$ cyclopentadienyl and substituted ones thereof.

Combination of carbon numbers participating in the bond of the two ligands to palladium in the palladium complex is preferably (three and three), (five and five) and (three and five), more preferably (three and three) and (three and five) and, most preferably (three and five). In those complexes, neutral organopalladium complexes may be connected by a connecting group.

When carbon numbers participating in the bond of the two organic ligands are 3 and 5, the neutral organopalladium complex is preferably represented by the formulae (I) to (IV).

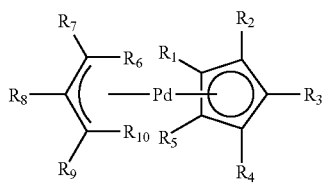

Formula (I)

In the formula, $R_1$, $R_2$, $R_3$, $R_4$, $R_5$, $R_6$, $R_7$, $R_8$, $R_9$ and $R_{10}$ each is hydrogen atom, halogen atom or a univalent organic group and may be bonded each other to form a ring structure. In the above formula, the ligand on the left side is an $\eta^3$ allyl ligand substituted with $R_6$, $R_7$, $R_8$, $R_9$ and $R_{10}$ and the ligand on the right side is an $\eta^5$ cyclopentadienyl ligand substituted with $R_1$, $R_2$, $R_3$, $R_4$ and $R_5$.

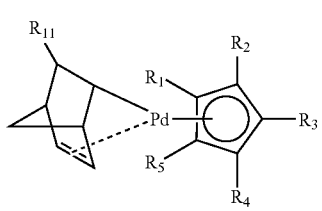

Formula (II)

In the formula, $R_1$, $R_2$, $R_3$, $R_4$, $R_5$ and $R_{11}$ each is hydrogen atom, halogen atom or a univalent organic group and may be bonded each other to form a ring structure. A dotted line means a coordination bond. In the above formula, the ligand on the right side is an $\eta^5$ cyclopentadienyl ligand substituted with $R_1$, $R_2$, $R_3$, $R_4$ and $R_5$.

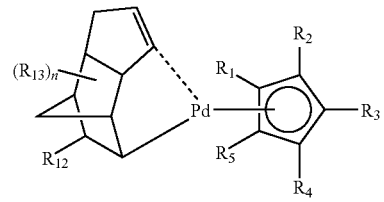

Formula (III)

In the formula, $R_1$, $R_2$, $R_3$, $R_4$, $R_5$, $R_{12}$ and $R_{13}$ each is hydrogen atom, halogen atom or a univalent organic group and may be bonded each other to form a ring structure; n is an integer of 1 to 12; $(R_{13})_n$ means that n $R_{13}$ group(s) is/are bonded; and a dotted line means a coordination bond. In the above formula, the ligand on the right side is an $\eta^5$ cyclopentadieny ligand substituted with $R_1$, $R_2$, $R_3$, $R_4$ and $R_5$.

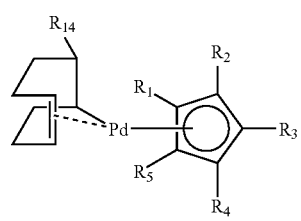

Formula (IV)

In the formula, $R_1$, $R_2$, $R_3$, $R_4$, $R_5$ and $R_{14}$ each is hydrogen atom, halogen atom or a univalent organic group and may be bonded each other to form a ring structure; and a dotted line means a coordination bond. In the above formula, the ligand on the right side is an $\eta^5$ cyclopentadienyl ligand substituted with $R_1$, $R_2$, $R_3$, $R_4$ and $R_5$.

When $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ each is a univalent organic group, its examples are as follows.

Thus, the examples thereof are an alkyl group (an alkyl group having 1 to 20 and, preferably, 1 to 10 carbons such as methyl, ethyl, isopropyl, tert-butyl, n-octyl, n-decyl, n-hexadecyl, cyclopropyl, cyclopentyl and cyclohexyl), an alkenyl group (an alkenyl group having 1 to 20 and, preferably, 1 to 10 carbons such as vinyl, allyl, 2-butenyl and 3-pentenyl), an alkynyl group (an alkynyl group having 1 to 20 and, preferably, 1 to 10 carbons such as propargyl and 3-pentynyl), an aryl group (an aryl group having 6 to 20 and, preferably, 6 to 15 carbons such as phenyl, p-methylphenyl, naphthyl, anthryl, phenanthryl and pyrenyl), an amino group (an amino group having 0 to 20 and, preferably, 0 to 10 carbons such as amino, methylamino, dimethylamino, diethylamino and dibenzylamino), an alkoxy group (an alkoxy group having 1 to 20 and, preferably, 1 to 10 carbons such as methoxy, ethoxy and butoxy), an aryloxy group (an aryloxy group having 6 to 20 and, preferably, 6 to 15 carbons such as phenyloxy and 2-naphthyloxy), a heterocyclic oxy group (a heterocyclic oxy group having 1 to 20 and, preferably, 1 to 10 carbons such as pyridyloxy, pyrimidinyloxy, pyridazinyloxy and benzimidazolyloxy), a silyoxy group (a silyoxy group having 3 to 20 and, preferably, 3 to 10 carbons such as trimethylsilyloxy and tert-butyldimethylsilyloxy), an acyl group (an acyl group having 1 to 20 and, preferably, 1 to 10 carbons such as acetyl, benzoyl, formyl and pivaloyl), an alkoxycarbonyl group (an alkoxycarbonyl group having 2 to 20 and, preferably, 2 to 10 carbons such as methoxycarbonyl and ethoxycarbonyl), an aryloxycarbonyl group (an aryloxycarbonyl group having 7 to 20 and, preferably, 7 to 15 carbons such as phenyloxycarbonyl), an acyloxy group (an acyloxy group having 1 to 20 and, preferably, 1 to 10 carbons such as acetoxy and benzoyloxy), an acylamino group (an acylamino group having 1 to 20 and, preferably, 1 to 10 carbons such as acetylamino and benzoylamino), an alkoxycarbonylamino group (an alkoxycarbonylamino group having 2 to 20 and, preferably, 2 to 10 carbons such as methoxycarbonylamino), an aryloxycarbonylamino group (an aryloxycarbonylamino group having 7 to 20 and, preferably, 7 to 15 carbons such as phenyloxycarbonylamino), an alkyl or arylsulfonylamino group (an alkyl or arylsulfonylamino group having 1 to 20 and, preferably, 1 to 10 carbons such as methanesulfonylamino and benzenesulfonylamino), a sulfamoyl group (a sulfamoyl group having 0 to 20 and, preferably, 0 to 10 carbons such as sulfamoyl, N-methylsulfamoyl, N,N-dimethylsulfamoyl and N-phenylsulfamoyl), a carbamoyl group having 1 to 20 and, preferably, 1 to 10 carbons such as carbamoyl, N-methylcarbamoyl, N,N-diethylcarbamoyl and N-phenylcarbamoyl), an alkylthio group (an alkylthio group having 1 to 20 and, preferably, 1 to 10 carbons such as methylthio and ethylthio), an arylthio group (an arylthio group having 6 to 20 and, preferably, 6 to 15 carbons such as phenylthio), a heterocyclic thio group (a heterocyclic thio group having 1 to 20 and, preferably, 1 to 10 carbons such as pyridinylthio, pyrimidinylthio, pyridazinylthio, benzimidazolylthio and thiadiazolylthio), an alkyl or arylsulfonyl group (an alkyl or arylsulfonyl group having 1 to 20 and, preferably, 1 to 10 carbons such as mesyl and tosyl), an alkyl or arylsulfinyl group (an alkyl or arylsulfinyl group having 1 to 20 and, preferably, 1 to 10 carbons such as methanesulfinyl and benzenesulfinyl), hydroxyl group, mercapto group, cyano group, sulfo group, carboxyl group, nitro group, hydroxamic acid group, sulfino group, hydrazino group, imino group, a heterocyclic group (a heterocyclic group having 1 to 20 and, preferably, 1 to 10 carbons such as that having nitrogen atom, oxygen atom and sulfur atom and, to be more specific, imidazolyl, pyridyl, quinolyl, furyl, thienyl, piperidyl, morpholino, benzoxazolyl, benzoimidazolyl, benzothiazolyl, carbazolyl, azepinyl, etc.) and a silyl group (a silyl group having 3 to 20 and, preferably, 3 to 10 carbons such as trimethylsilyl and triphenylsilyl). Such an organic group may be further substituted. When there are two or more substituents, they may be same or different. Further, in case it is possible, they may be connected each other to form a ring.

With regard to $R_1$, $R_2$, $R_3$, $R_4$, $R_5$, $R_6$, $R_7$, $R_8$, $R_9$, $R_{10}$ and $R_{13}$, preferred ones are hydrogen atom, methyl group, trimethylsilyl group and phenyl group, more preferred ones are hydrogen atom and methyl group and a particularly preferred one is hydrogen atom.

With regard to $R_{11}$, $R_{12}$ and $R_{14}$, preferred ones are an alkoxy group and an aryloxy group, more preferred one is an alkoxy group and the most preferred one is methoxy group.

n is an integer of 1 to 12 and, when $R_{13}$ is other than hydrogen atom, it is preferably 1 to 10, more preferably 1 to 5 and, most preferably, 1 to 2.

Specific examples of the palladium complex of the present invention are as follows although they are non-limitative.

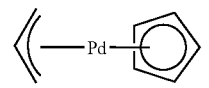

1

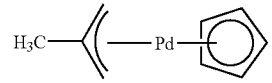

2

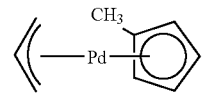

3

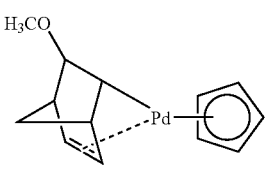

4

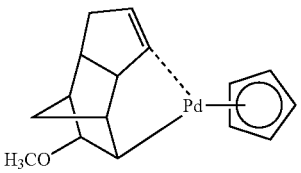

5

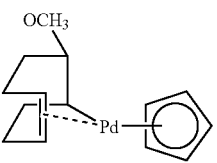

6

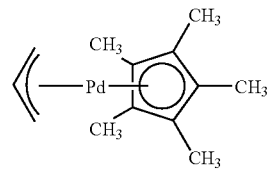

7

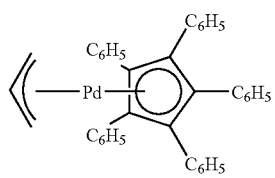

8

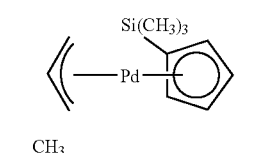

9

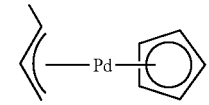

10

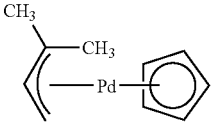

11

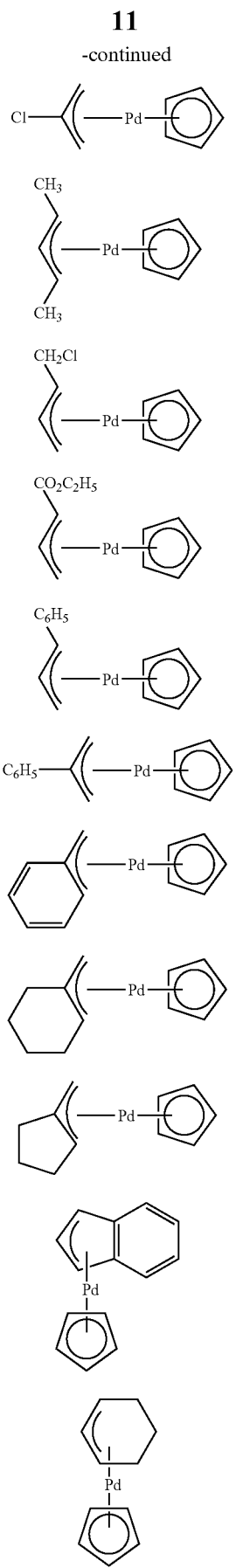
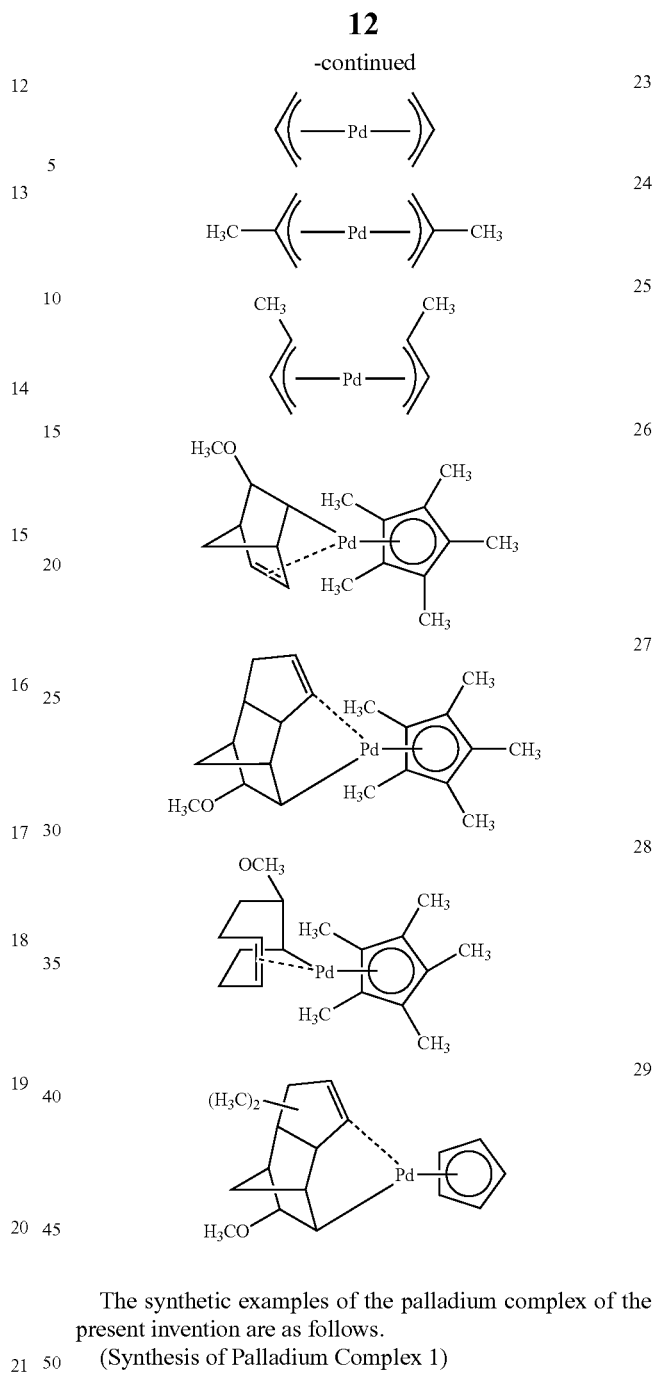

The synthetic examples of the palladium complex of the present invention are as follows.

(Synthesis of Palladium Complex 1)

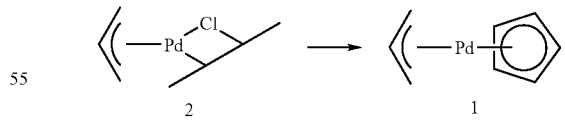

An allyl palladium chloride dimer (1.00 g) (manufactured by Tokyo Kasei) and 15 mL of dehydrated tetrahydrofuran were added into a flask made of glass where inner air was substituted with highly pure argon. A 2.0 M solution (2.9 mL) of cyclopentadienyl sodium in tetrahydrofuran (manufactured by Aldrich) was dropped into the above-prepared yellow suspension with stirring in an ice bath and was stirred for 5 minutes. The reaction mixture was returned to room temperature and 1 mL of methanol was added thereto. The solvent was evaporated without contacting to the air. Hexane (50 mL) was added to the resulting residue to give a red solution. This was filtered and the resulting filtrate was cooled on a dry ice bath. The supernatant liquid was subjected to decantation and the resulting red crystals were dried in vacuo. Red crystals of 1 were obtained in 825 mg. Data by $^1$H-NMR thereof were identical with those of a literature (*Journal of Chemical Society, Dalton Transaction*, 1973, page 2390).

(Synthesis of Palladium Complex 2)

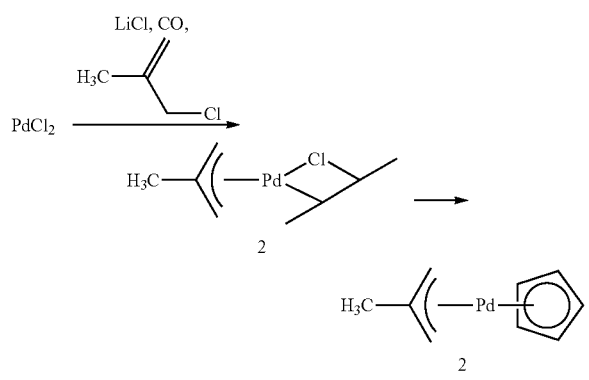

Palladium chloride (2.00 g; manufactured by Wako Pure Chemical Industry), 1.9 g of lithium chloride (manufactured by Wako Pure Chemical Industry) and 40 mL methanol were added into a flask made of glass where inner air was substituted with highly pure argon and were stirred for 4 hours. To the resulting homogeneous solution was added 1.62 g of 3-chloro-2-methyl-1-propene (manufactured by Wako Pure Chemical Industry) and carbon dioxide was bubbled thereinto for 4 hours. The resulting yellow solution was evaporated at low temperature. The yellow residue was extracted with methylene chloride and the extract was filtered. The filtrate was concentrated using an evaporator followed by adding hexane thereto whereupon 1.72 g of yellow 2-methylallyl palladium chloride dimer crystals were prepared.

From the above-mentioned 2-methylallyl palladium chloride dimer (1.08 g) were prepared 895 mg of the red crystals of 2 by the same operation as in the synthetic formulation for 1. Data thereof by $^1$H-NMR were identical with those in a literature (*Journal of Chemical Society, Dalton Transaction*, 1973, page 2390).

(Synthesis of Palladium Complex 3)

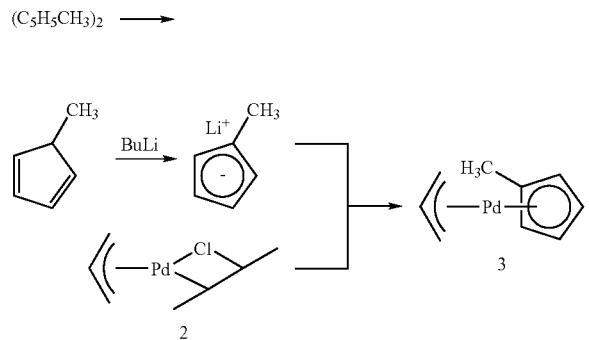

Methylcyclopentadiene dimer (50 mL; manufactured by Wako Pure Chemical Industry) was heated at 180 to 200° C. to give methylcyclopentadiene. This compound (0.52 g) was charged in a flask made of glass where inner air was substituted with highly pure argon and 5 mL of dehydrated tetrahydrofuran was added thereto. The flask was cooled on an ice bath and 4.1 mL of 1.6 M solution of butyl lithium in hexane (manufactured by Wako Pure Chemical Industry) was added thereto. To the resulting red solution was added 1.00 g of allyl palladium chloride dimer and the mixture was stirred for 5 minutes. The reaction mixture was returned to room temperature and 1 mL of methanol was added thereto. The solvent was evaporated without contacting to the air. To the resulting residue was added 50 mL of hexane to give a red solution. This was filtered and the resulting filtrate was cooled on a dry ice bath. The supernatant liquid was subjected to decantation and the resulting red crystals were dried in vacuo to give 805 mg of red crystals of 3. The $^1$H-NMR data thereof were identical with those in the literature (*Nature Forschung*, B 1984, volume 39, page 990).

(Synthesis of Palladium Complex 4)

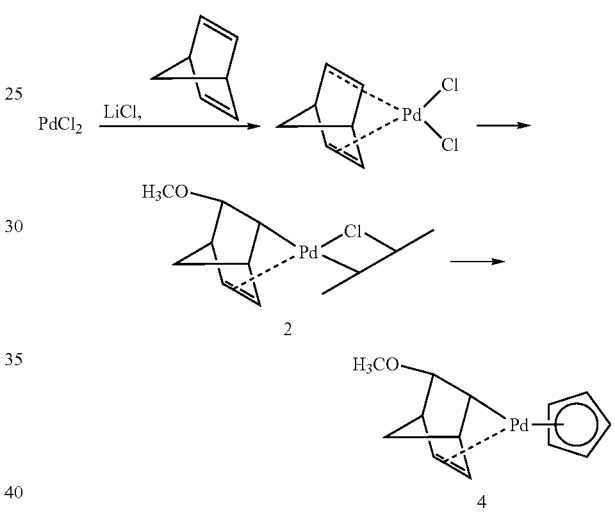

Palladium chloride (3.00 g; manufactured by Wako Pure Chemical Industry), 2.10 g of lithium chloride (manufactured by Wako Pure Chemical Industry) and 40 mL of methanol were charged in a flask made of glass where the inner air was substituted with highly pure argon and were stirred for 4 hours. Norbornadiene (2.1 g; manufactured by Aldrich) was added to the resulting homogeneous solution and the mixture was stirred for 12 hours. The resulting yellow solid was sucked to give 3.6 g of norbornadiene dichloropalladium.

The above-prepared norbornadiene dichloropalladium (1.40 g) was added to 20 mL of methanol in a flask made of glass where inner air was substituted with highly pure argon and then the inner temperature was made −40° C. using a dry ice bath. Into this was dropped 1.5 mL of a 28% methanolic solution of sodium methoxide (manufactured by Wako Pure Chemical Industry). The mixture was made to react for 1 hour and returned to room temperature. The resulting yellow solid was sucked and washed with methanol to give 1.22 g of methoxynorbornene palladium chloride dimer.

From the above-prepared 1.20 g of methoxynorbornene palladium chloride dimer were prepared 1020 mg of red crystals of 4 by the same operation as in the synthetic formulation for 1.

(Synthesis of Palladium Complex 5)

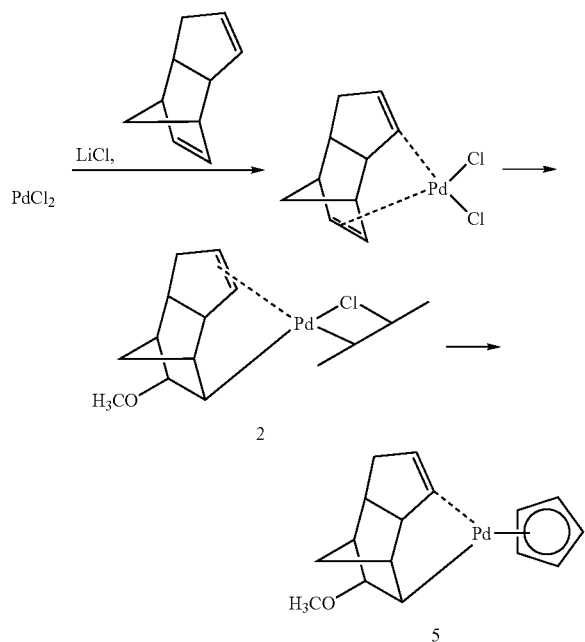

Palladium chloride (3.00 g; manufactured by Wako Pure Chemical Industry), 2.10 g of lithium chloride (manufactured by Wako Pure Chemical Industry) and 40 mL of methanol were charged in a flask made of glass where inner air was substituted with highly pure argon and were stirred for 4 hours. Dicyclopentadiene (3.06 g; manufactured by Wako Pure Chemical Industry) was added to the resulting homogeneous solution and the mixture was stirred for 12 hours. The resulting yellow solid was sucked to give 4.84 g of dicyclopentadiene dichloropalladium.

From 4.50 of the above-prepared dicyclopentadiene dichloropalladium were prepared 3.10 g of red crystals of 5 by the same operation as in the synthetic formulation for 4. The $^1$H-NMR data thereof were identical with those in the literature (*Journal of the American Chemical Society*, 1966, volume 88, page 5135).

(Synthesis of Palladium Complex 6)

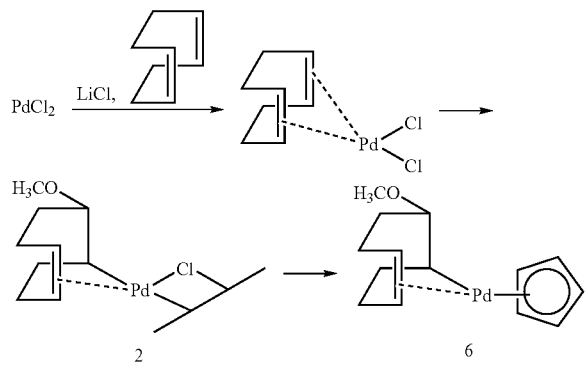

Palladium chloride (3.0 g; manufactured by Wako Pure Chemical Industry), 2.1 g of lithium chloride (manufactured by Wako Pure Chemical Industry) and 40 mL of methanol were charged in a flask made of glass where inner air was substituted with highly pure argon and were stirred for 4 hours. 1,5-Cyclooctadiene (2.31 g; manufactured by Wako Pure Chemical Industry) was added to the resulting homogeneous solution and the mixture was stirred for 12 hours. The resulting yellow solid was sucked to give 4.82 g of 1,5-cyclooctadiene dichloropalladium.

From 3.50 of the above-prepared 1,5-cyclooctadiene dichloropalladium were prepared 1.23 g of red crystals of 6 by the same operation as in the synthetic formulation for 4. The $^1$H-NMR data thereof were identical with those in the literature (*Journal of the Chemical Society*, 1964, page 5002.

(b) Organophosphorus Compounds

The organophosphorus compound used in the present invention has one phosphorus atom in a molecule and has an action of causing a mono dentate coordination to the neutral organopalladium complex of (a). When a catalytically active species is generated, the organophosphorus compound is coordinated to palladium and, therefore, it inhibits the coordination of the polar group of the polar group-containing norbornene to palladium whereby it makes the polymerization to proceed. Therefore, such an inhibition is insufficient unless the organophosphorus compound is well bulky whereby polymerization does not proceed. On the other hand, when the organophosphorus compound is too bulky, the polar group-containing norbornene is not coordinated to and inserted into palladium whereby polymerization does not proceed as well. Accordingly, an appropriate bulkiness is necessary for the organophosphorus compound.

The organophosphorus compound having one phosphorus atom used in the present invention is preferably a trivalent organophosphorus compound having three organic groups. To be more specific, it is a phosphine compound or a phosphite compound, preferably a tertiary phosphine compound or phosphite compound, still more preferably dialkyl aryl phosphine, diaryl alkyl phosphine, trialkyl phosphine, triaryl phosphine, trialkyl phosphite or triaryl phosphite and, most preferably, triaryl phosphine or trialkyl phosphine.

Examples of the phosphine compound used in the present invention are as follows although they are non-limitative. Preferred phosphine compounds are triphenyl phosphine, tritolyl phosphine, methyl diphenyl phosphine, ethyl diphenyl phosphine, dimethyl phenyl phosphine, dioctyl phenyl phosphine, tridecanyl phosphine, trinonyl phosphine, trioctyl phosphine, triheptyl phosphine, trihexyl phosphine, tripentyl phosphine, tributyl phosphine, tripropyl phosphine, triethyl phosphine, trimethyl phosphine, dimethyl octyl phosphine, dioctyl methyl phosphine, dimethyl heptyl phosphine, diheptyl methyl phosphine, dimethyl hexyl phosphine, dihexyl methyl phosphine, dimethyl butyl phosphine, dibutyl methyl phosphine, tripentyl phosphine, tricyclohexyl phosphine, triheptyl phosphine, tribenzyl phosphine, dimethyl cyclohexyl phosphine and dicyclohexyl methyl phosphine.

Among them, preferred ones in view of easy synthesis and easy handling are compounds of a triaryl phosphine type and compounds of a trialkyl phosphine type, more preferred ones are triphenyl phosphine, tributyl phosphine and tricyclohexyl phosphine and the most preferred ones are triphenyl phosphine and tricyclohexyl phosphine.

(c) Salt Comprising Counter-Cation and Anion Having No Unshared Electron Pair in the Central Atom The salt used in the present invention comprises anion and cation and the anion has no unshared electron pair in the central atom. Therefore, this anion has a property of non-coordinating or of weakly coordinating to palladium atom of (a) and is also called a non-coordinating or weakly coordinating anion. When (c) is added to a mixture of (a) and (b), neutral organopalladium complex is converted to cationic organopalladium complex. In order to enhance the cationic property of the palladium complex, it is necessary to enhance the charge of anion. Accordingly, it is preferred that anion contains fluorine or the like having a high electro-negativity. In addition, in order to weaken the coordination of anion to palladium, it is preferred to make the anion molecule bulky. As a result of such a design, polar group-containing norbornene is apt to be coordinated to the generated cationic palladium complex and the succeeding insertion becomes easy whereby a polymerizing activity is enhanced. With regard to examples of such an anion, there are anions of a substituted borate type and of a substituted aluminate type and the following examples are listed.

Examples of a borate are tetrakis(pentafluorophenyl) borate, tetrakis(3,5-bis(trifluoromethyl)phenyl) borate, tetrakis(2-fluorophenyl) borate, tetrakis(3-fluorophenyl) borate, tetrakis(3,5-difluorophenyl) borate, tetrakis(2,3,4,5-tetrafluorophenyl) borate, tetrakis(3,4,5,6-tetrafluorophenyl) borate, tetrakis(3,4,5-trifluorophenyl) borate, methyl tris(perfluorophenyl) borate, ethyl tris(perfluorophenyl) borate, phenyl tris(perfluorophenyl) borate, tetrakis(1,2,2-trifluoroethylenyl) borate, tetrakis(4-tri-isopropylsilyltetrafluorophenyl) borate, tetrakis(4-dimethyl-tert-butylsilyltetrafluorophenyl) borate, (triphenylsiloxy) tris(pentafluorophenyl) borate, (octyloxy) tris(pentafluorophenyl) borate, tetrakis[3,5-bis[1-methoxy-2,2,2-trifluoro-1-(trifluoro-methyl)ethyl]phenyl] borate, tetrakis[3-[1-methoxy-2,2,2-trifluoro-1-(trifluoromethyl)ethyl]-5-(trifluoromethyl)-phenyl] borate and [3-(2,2,2-trifluoro-1-(2,2,2-trifluoro-ethoxy)-1-(trifluoromethyl)ethyl)-5-(trifluoromethyl)-phenyl] borate although they are non-limitative.

Examples of the aluminate are tetrakis(pentafluoro-phenyl) aluminate, tris(nonafluorobiphenyl) fluoroaluminate, (octyloxy) tris(pentafluorophenyl) aluminate, tetrakis(3,5-bis(trifluoromethyl)phenyl) aluminate and methyl tris(pentafluorophenyl) aluminate although they are non-limitative.

The counter-cation to the anion may be anything such as alkali metal cation, alkali earth metal cation and organic cation and preferred ones are alkali metal ion ($Li^+$, $Na^+$ and $K^+$), N,N-dialkylanilinium ion and trityl cation.

A salt by combination of the above-mentioned anion and cation is (c) of the present invention and its examples are as follows.

Lithium tetrakis(2-fluorophenyl) borate, sodium tetrakis(2-fluorophenyl) borate, lithium tetrakis(3-fluorophenyl) borate, sodium tetrakis(3-fluorophenyl) borate, ferrocenium tetrakis(3-fluorophenyl) borate, ferrocenium tetrakis(pentafluorophenyl) borate, lithium tetrakis(4-fluorophenyl) borate, sodium tetrakis(4-fluorophenyl) borate, lithium tetrakis(3,5-difluorophenyl) borate, sodium tetrakis(3,5-difluorophenyl) borate, trityl tetrakis(3,5-difluorophenyl) borate, 2,6-dimethylanilinium tetrakis(3,5-difluorophenyl) borate, lithium tetrakis(pentafluorophenyl) borate, lithium (diethyl ether) tetrakis(pentafluorophenyl) borate, lithium (diethyl ether)$_{2.5}$ tetrakis(pentafluorophenyl) borate, lithium tetrakis(2,3,4,5-tetrafluorophenyl) borate, lithium tetrakis(3,4,5,6-tetrafluorophenyl) borate, lithium tetrakis(1,2,2-trifluorophenyl) borate, lithium tetrakis(3,4,5-trifluorophenyl) borate, lithium methyl tris(perfluorophenyl) borate, lithium phenyl tris(perfluorophenyl) borate, lithium tris(isopropanol) tetrakis(pentafluorophenyl) borate, lithium tetrakis(methanol) tetrakis(pentafluorophenyl) borate, trityl tetrakis(pentafluorophenyl) borate, trityl tetrakis(4-triisopropylsilyltetrafluorophenyl) borate, trityl tetrakis(4-dimethylsilyltetrafluorophenyl) borate, N,N-dimethylanilinium tetrakis(pentafluorophenyl) borate, N,N-dimethylanilinium tetrakis[3,5-bis(trifluoromethyl)phenyl] borate, lithium (triphenylsiloxy) tris(pentafluorophenyl) borate, sodium (triphenyl)siloxy) tris(pentafluorophenyl) borate, sodium tetrakis(2,3,4,5-tetrafluorophenyl) borate, sodium tetrakis(3,4,5,6-tetrafluorophenyl) borate, sodium tetrakis(1,2,2-trifluoroethylenyl) borate, sodium tetrakis(3,4,5-trifluorophenyl) borate, sodium methyl tris(perfluorophenyl) borate, sodium phenyl tris(perfluorophenyl) borate, sodium methyl tris(perfluorophenyl) borate, trityl tetrakis(2,3,4,5-tetrafluorophenyl) borate, trityl tetrakis(3,4,5,6-tetrafluorophenyl) borate, trityl tetrakis(1,2,2-trifluorophenyl) borate, trityl tetrakis(3,4,5-trifluorophenyl) borate, trityl methyl tris(perfluorophenyl) borate, trityl phenyl tris(perfluorophenyl) borate, lithium hexyl tris(pentafluorophenyl) borate, lithium triphenylsiloxy tris(pentafluorophenyl) borate, lithium (octyloxy) tris(pentafluorophenyl) borate, lithium tetrakis(3,5-bis(trifluoromethyl)phenyl) borate, sodium tetrakis(pentafluorophenyl) borate, sodium (octyloxy) tris(pentafluorophenyl) borate, sodium tetrakis(3,5-bis(trifluoromethyl)phenyl) borate, lithium tetrakis[3,5-bis[1-methoxy-2,2,2-trifluoro-1-(trifluoro-methyl)ethyl]phenyl] borate, sodium tetrakis[3,5-bis[1-methoxy-2,2,2-trifluoro-1-(trifluoro-methyl)ethyl]phenyl] borate, lithium tetrakis[3-[1-methoxy-2,2,2-trifluoro-1-(trifluoromethyl)ethyl]-5-(trifluoromethyl)phenyl] borate, sodium tetrakis[3-[1-methoxy-2,2,2-trifluoro-1-(trifluoromethyl)ethyl]-5-(trifluoromethyl)phenyl] borate, lithium tetrakis[3-[2,2,2-trifluoro-1-(2,2,2-trifluoroethoxy)-1-(trifluoro-methyl)ethyl]-5-(trifluoromethyl)phenyl] borate, sodium tetrakis[3-[2,2,2-trifluoro-1-(2,2,2-trifluoroethoxy)-1-(trifluoromethyl)ethyl]-5-(trifluoromethyl)phenyl] borate, trimethylsilylium tetrakis(pentafluorophenyl) borate, trimethylsilylium etherate tetrakis(pentafluorophenyl) borate, triethylsilylium tetrakis(pentafluorophenyl) borate, triphenylsilylium tetrakis(pentafluorophenyl) borate, tris(mesityl)silylium tetrakis(pentafluorophenyl) borate, tribenzylsilylium tetrakis(pentafluorophenyl) borate, triethylsilylium tetrakis(pentafluorophenyl) borate, triphenylsilylium tetrakis(pentafluorophenyl) borate, tribenzylsilylium tris(pentafluorophenyl) borate, trimethylsilylium tetrakis(2,3,4,5-tetrafluorophenyl) borate, triethylsilylium tetrakis(2,3,4,5-tetrafluorophenyl) borate, triphenylsilylium tetrakis(2,3,4,5-tetrafluorophenyl) borate, tribenzylsilylium tetrakis(2,3,4,5-tetrafluorophenyl) borate, trimethylsilylium tetrakis(2,3,4,5-tetrafluorophenyl) borate, triphenylsilylium tetrakis(2,3,4,5-tetrafluorophenyl) borate, trimethylsilylium tetrakis(3,4,5-trifluorophenyl) borate, tribenzylsilylium tetrakis(3,4,5-trifluorophenyl) borate, triphenylsilylium tetrakis(3,4,5-trifluorophenyl) borate, triethylsilylium tetrakis(1,2,2-trifluorophenyl) borate, tricyclohexylsilylium tetrakis(2,3,4,5-tetrafluorophenyl) borate, dimethyloctadecylsilylium tetrakis(pentafluoro-phenyl) borate, tris(trimethylsilyl) silylium methyl tris(2,3,4,5-tetrafluorophenyl) borate, 2,2'-dimethyl-1,1'-binaphthyl methyl tetrakis(3,4,5-trifluorophenyl) borate, lithium tetrakis(pentafluorophenyl) aluminate, trityl (perfluorobifluorophenyl) fluoroaluminate, lithium (octyloxy) tris(pentafluorophenyl) aluminate, lithium tetrakis(3,5-bis(trifluoromethyl)phenyl) aluminate, sodium tetrakis(pentafluorophenyl) aluminate, trityl tetrakis(pentafluorophenyl) aluminate, sodium (octyloxy) tris (pentafluorophenyl) aluminate, sodium tetrakis(3,5-bis(trifluoromethyl)phenyl) aluminate and trityl tetrakis(pentafluorophenyl) aluminate although they are non-limitative.

Among the above, in view of easy synthesis and easy handling, preferred ones are salts of a borate type, more preferred ones are salts of a tetrakis(pentafluorophenyl) borate type and the most preferred ones are trityl tetrakis (pentafluorophenyl) borate, N,N-dimethylanilinium tetrakis (pentafluorophenyl) borate, lithium tetrakis(pentafluorophenyl) borate and sodium tetrakis(pentafluorophenyl) borate.

(Catalyst for Polymerization of Polar Group-Containing Norbornene)

In the present invention, the aforementioned organometallic compound in which (a), (b) and (c) are mixed is able to be used as a catalyst for polymerization of polar group-containing norbornene. Those (a), (b) and (c) react and give a catalytically active species which is a cationic palladium complex. (b) is coordinated to palladium of (a) and, if two or more molecules are coordinated, the polar group-containing norbornene is unable to be coordinated and polymerization does not proceed. Therefore, amount of (b) to (a) is preferably 0.1 to 1.9 equivalent(s), more preferably 0.3 to 1.5 equivalent(s) and, most preferably, 0.5 to 1.3 equivalent(s). (c) exchanges the anion of the catalytically active species to give a palladium cation complex. Charge of this cation complex is univalent or divalent. Accordingly, amount of (c) to (a) is preferably 0.1 to 10 equivalent(s), more preferably 0.5 to 5 equivalent(s) and, most preferably, 1 to 5 equivalent(s).

In the present invention, (a), (b) and (c) are mixed and the resulting uniform solution is used as a catalytically active species. When the polar group-containing norbornene is liquid and is able to dissolve (a), (b) and (c) therein, they may be mixed in the polar group-containing norbornene. In the case of mixing in a solvent, there may be a case where the solvent is coordinated to palladium and lowers the activity of the catalyst. Therefore, the solvent is preferred to be nonpolar or lowly polar, and toluene may be exemplified therefor. Since (c) is a salt, there may be a case where it is not soluble in nonpolar or lowly polar solvent and, in that case, it may be dissolved in a lowly polar solvent of a halogen type such as methylene chloride and then mixed.

In the catalytic system used in the present invention, yellowish color of the polymer becomes deep when amount of the catalyst is high while, when the amount is low, the reaction becomes time-consuming or the yield decreases. Therefore, amount of palladium to 1 equivalent of the monomer is preferably 1/1,000,000 to 1/1,000 equivalent, more preferably 1/100,000 to 1/1,000 equivalent and, most preferably, 1/100,000 to 1/5,000 equivalent.

(Polar Group-Containing Norbornene)

The polar group-containing norbornene of the present invention has at least one polar group in a norbornene ring and is represented by the following formula (C).

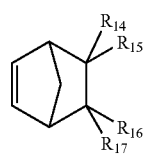

Formula (C)

In the formula, $R_{14}$, $R_{15}$, $R_{16}$ and $R_{17}$ each is hydrogen atom, halogen atom or a univalent organic group and may be bonded each other to form a ring structure. At least one of $R_{14}$, $R_{15}$, $R_{16}$ and $R_{17}$ is a univalent organic group and at least one of the organic group(s) is a polar group.

A polar group is an organic group in which polarization takes place by an atom having a high electronegativity such as oxygen, sulfur, nitrogen and halogen. Specific examples thereof are an amino group (an amino group having 1 to 20 or, preferably, 1 to 10 carbon(s) such as amino, methylamino, dimethylamino, diethylamino and dibenzylamino), an alkoxy group (an alkoxy group having 1 to 20 or, preferably, 1 to 10 carbon(s) such as methoxy, ethoxy and butoxy), an aryloxy group (an aryloxy group having 6 to 20 or, preferably, 6 to 15 carbons such as phenyloxy and 2-naphthyloxy), a heterocyclic oxy group (a heterocyclic oxy group having 1 to 20 or, preferably, 1 to 10 carbon(s) such as pyrrolidinyloxy, pyrimidinyloxy, pyridazinyloxy and benzimidazolyloxy), a silyloxy group (a silyloxy group having 3 to 20 or, preferably, 3 to 10 carbons such as trimethylsilyloxy and tert-butylsilyloxy), an acyl group (an acyl group having 1 to 20 or, preferably, 1 to 10 carbon(s) such as acetyl, benzoyl, formyl and pivaloyl), an alkoxycarbonyl group (an alkoxycarbonyl group having 2 to 20 or, preferably, 2 to 10 carbons such as methoxycarbonyl and ethoxycarbonyl), an aryloxycarbonyl group (an aryloxycarbonyl group having 6 to 20 or, preferably, 6 to 15 carbons such as phenyloxycarbonyl), an acyloxy group (an acyloxy group having 1 to 20 or, preferably, 1 to 10 carbon(s) such as such as acetoxy and benzoyloxy), an acylamino group (an acylamino group having 1 to 20 or, preferably, 1 to 10 carbon(s) such as acetylamino and benzoylamino), an alkoxycarbonylamino group (an alkoxycarbonyl amino group having 2 to 20 or, preferably, 2 to 10 carbons such as methoxycarbonylamino), an aryloxycarbonylamino group (an aryloxycarbonylamino group having 6 to 20 or, preferably, 6 to 15 carbons such as phenyloxycarbonylamino), an alkyl or arylsulfonylamino group (an alkyl or arylsulfonylamino group having 1 to 20 or, preferably, 1 to 10 carbon(s) such as such as methanesulfonylamino and benzenesulfonylamino), a sulfamoyl group (a sulfamoyl group having 0 to 20 or, preferably, 0 to 10 carbon(s) such as sulfamoyl, N-methylsulfamoyl, N,N-dimethylsulfamoyl and N-phenylsulfamoyl), a carbamoyl group (a carbamoyl group having 1 to 20 or, preferably, 1 to 10 carbon(s) such as carbamoyl, N-methylcarbamoyl, N,N-diethylcarbamoyl and N-phenylcarbamoyl), a ureido group (a ureido group having 1 to 20 or, preferably, 1 to 10 carbon(s) such as ureido, methylureido and phenylureido), hydroxyl group, halogen atom (such as fluorine atom, chlorine atom, bromine atom and iodine atom), cyano group, sulfo group, imino group and heterocyclic group. Such a substituent may be directly connected to a norbornene ring, may be connected via an alkylene group or the like or may be further substituted. When there are two or more substituents, they may be same or different. In case it is possible, they may be connected each other to form a ring. With regard to the polar group, preferred ones are an amino group, an alkoxy group, an aryloxy group, a heterocyclic oxy group, a silyloxy group, an acyl group, an alkoxycarbonyl group, an aryloxycarbonyl group, an acyloxy group, an acylamino group, an alkoxycarbonylamino group and an aryloxycarbonylamino group and more preferred ones are an alkoxycarbonyl group, an acyloxy group, an acylamino group and an alkoxycarbonylamino group.

Specific examples of the polar group-containing norbornene of the present invention are the following compounds although they are non-limitative.

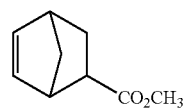

M-1

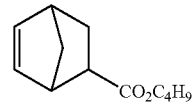

M-2

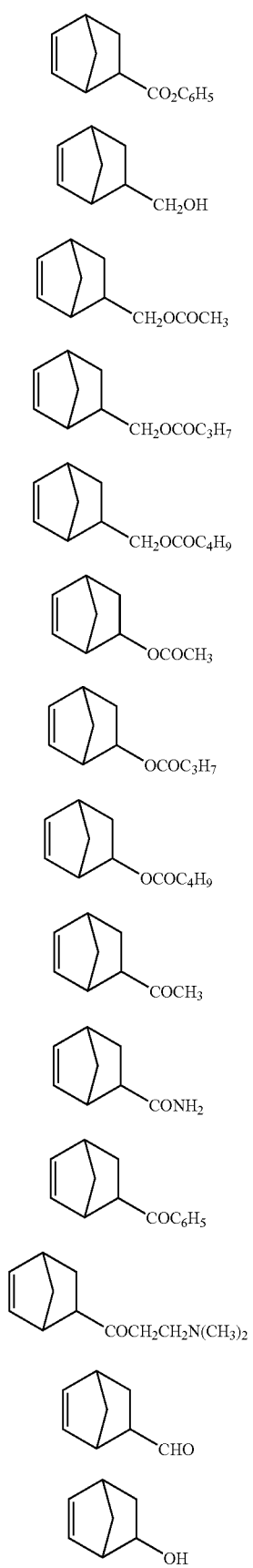
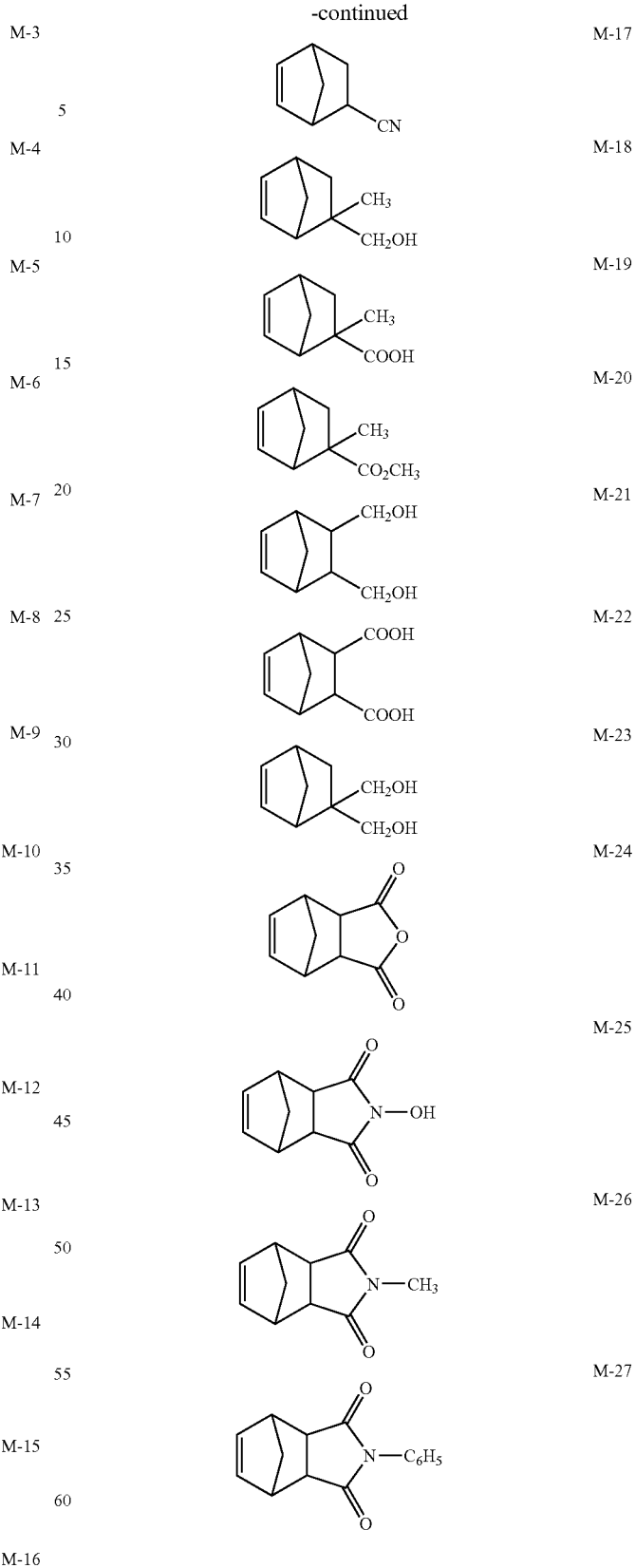
(Monomers for Polymerization)
The monomer for polymerization according to the present invention always contains a polar group-containing norbornene and it is also possible to copolymerize as a mixture of two or more of the aforementioned polar group-containing norbornenes. It is further possible to copolymerize with a norbornene containing no polar group such as arylnorbornene, alkylnorbornene and norbornene and with a cyclic olefin other than norbornene or an aliphatic olefin.

Catalytic activity of the polymerization catalyst system of the present invention may lower by impurities in air, water or monomer and, therefore, the monomer for polymerization as such is preferred to be purified by distillation or recrystallization before use. Purity of the monomer is preferably 95 to 100%, more preferably 98 to 100% and, still more preferably, 99 to 100%.

(Environment for Polymerization Reaction)

In the catalyst system of the present invention, catalyst may be inactivated by air or water whereupon polymerizing property lowers or no polymerization proceeds. Accordingly, it is preferred to be operated in an atmosphere of highly pure inert gas.

(Solvents for Polymerization Reaction)

When the polar group-containing norbornene is liquid and is able to dissolve (a), (b) and (c), it is also possible that they are mixed without solvent and made to react neatly. However, as the reaction proceeds, viscosity increases and stirring may become difficult and, therefore, it is desirable to use a solvent. With regard to a solvent, a lowly polar solvent which is hardly coordinated to the catalyst is preferred. A solvent which is able to dissolve all of the catalyst, the polar group-containing norbornene and the resulting addition polymer of polar group-containing norbornene is more preferred. Examples of such a solvent are aromatic hydrocarbons such as benzene, toluene, xylene, cumene, p-cymene and mesitylene where preferred ones are toluene and xylene and still more preferred one is toluene.

On the other hand, when polarity of the solvent is too low, the polar group-containing norbornene or the polar group-containing norbornene polymer is unable to be dissolved. Therefore, it is necessary to use an appropriate solvent depending upon the polar group-containing norbornene used. In that case, an appropriate polar solvent may be added to the abovementioned lowly polar solvent. Examples of such a polar solvent are methylene chloride and dichloroethane.

The solvent is added to the polar group-containing norbornene in an amount of 0 to 50 part(s) by mass, preferably 0.3 to 20 part(s) by mass and, still more preferably, 0.5 to 5 part(s) by mass. (In this specification, mass ratio is equal to weight ratio.)

When the solvent is contaminated with air or water, the catalyst is inactivated and the polymerizing property may lower or the polymerization may not proceed. Therefore, when a solvent is used, it is preferred to subject to dehydrating distillation and deaeration before use.

(Temperature for Polymerization Reaction)

Although the polymerization reaction of the present invention proceeds even at the temperature which is lower than room temperature, the reaction is able to be accelerated by heating. However, too much heating causes decomposition of the catalytically active species. Therefore, temperature for the reaction is preferably from room temperature to 150° C., more preferably 50 to 130° C. and, most preferably, 70 to 120° C.

(Reaction Time for Polymerization Reaction)

Although reaction time of the polymerization reaction of the present invention is dependent upon reaction temperature, amount of the solvent, type of the polar group-containing norbornene, etc., the reaction is able to be finished within several tens minutes to ten-odd hours. Finish of the reaction is able to be judged by generation of palladium black in the reaction solution and, since the reaction time may become long, it is desired to finish appropriately.

(After-Treatment of Polymerization Reaction)

After stopping the heating of the reaction solution, the reaction as it is or after diluting with an appropriate solvent is mixed with a poor solvent (such as a solvent of an alcohol type, e.g. methanol) whereupon a solid in white to yellowish white color is obtained. This is filtered and dried in vacuo to give a polar group-containing norbornene polymer. When yellowish color of the polymer is too strong, residual divalent palladium is able to be made into palladium black when an appropriate reducing agent is used and, when it is removed by filtration, a white polymer is able to be prepared.

Further, as to the second object of the present invention, the present inventor has confirmed that, in a polymerization reaction of a norbornene compound, the resulting polymer is colored when the catalyst disclosed in Papers to be presented at the 85th Spring Meeting of the Chemical Society of Japan, 1PA-019 and Papers to be presented at the 54th Annual Meeting of the Polymer Society, 1Pe-037 is used. As a result of intensive investigations for solving the coloring phenomenon, it has been found that polymers where coloration is suppressed are prepared when an organometallic complex catalyst which is prepared by combination of a neutral organic palladium complex with a compound containing no trityl group and having a proton-donating trisubstituted ammonium is acted as a polymerization catalyst. In addition, it has been unexpectedly found that the catalytic system gives a high polymerization activity and, in the palladium complex to be combined, it has universality not only to allylcyclopentadienyl palladium but also to a neutral organopalladium complex having two organic ligands where carbons participating in the bonding to palladium are at least three. The present invention relating to the means for solving the second object will be illustrated in detail as hereunder.

(Norbornene Compound)

In the process for production of polymers of a norbornene according to the present invention, a norbornene compound represented by the following formula (A) is used as a material.

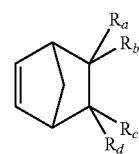

Formula (A)

In the formula, $R_a$, $R_b$, $R_c$ and $R_d$ each is hydrogen atom or a univalent organic group comprising carbon atom and hydrogen atom and may be bonded each other to form a ring structure.

Specific examples of the univalent organic group comprising carbon atom and hydrogen atom are an alkyl group (where carbon number(s) is/are preferably 1 to 20, more preferably 1 to 12 and, particularly preferably, 1 to 8 such as methyl, ethyl, isopropyl, tert-butyl, n-hexyl, n-octyl, n-decyl, n-hexadecyl, cyclopropyl, cyclopentyl and cyclohexyl), an alkenyl group (where carbon numbers are preferably 2 to 20, more preferably 2 to 12 and, particularly preferably, 2 to 8 such as vinyl, allyl, 2-butenyl and 3-pentenyl), an alkynyl group (where carbon numbers are preferably 2 to 20, more preferably 2 to 12 and, particularly preferably, 2 to 8 such as propargyl and 3-pentynyl) and an aryl group (where carbon numbers are preferably 6 to 30, more preferably 6 to 20 and, particularly preferably, 6 to 12 such as phenyl, p-methylphenyl, naphthyl, anthryl, phenanthryl and pyrenyl).

Specific examples of the norbornene compound represented by the formula (A) are the following compounds although the present invention is not limited by them.

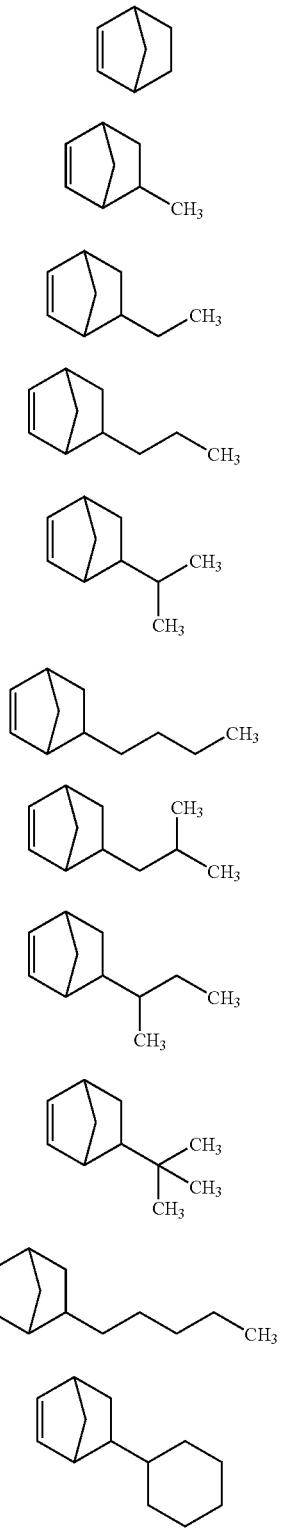

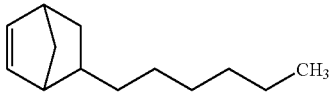

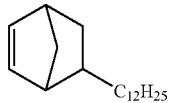

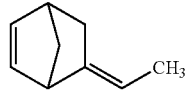

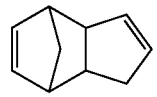

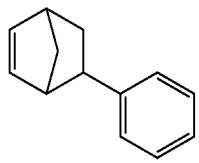

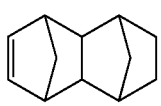

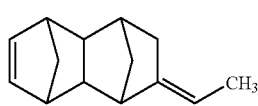

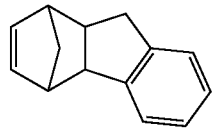

The norbornene compound represented by the formula (A) is able to be synthesized by conventional methods and, for example, it is able to be synthesized by the reaction of cyclopentadiene or dicyclopentadiene with the corresponding olefin.

In accordance with the process for production of polymers of the norbornene compound, it is also possible to prepare a copolymer where the compound represented by the above formula (A) is copolymerized with the compound represented by the following formula (B).

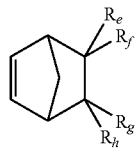

Formula (B)

In the formula, $R_e$, $R_f$, $R_g$ and $R_h$ each is hydrogen atom, halogen atom or a univalent organic group and may be bonded each other to form a ring structure. At least one of $R_e$, $R_f$, $R_g$ and $R_h$ is a univalent organic group and at least one of said organic group is a polar group.

A polar group is an organic group in which polarization takes place by an atom having a high electronegativity such as oxygen, sulfur, nitrogen and halogen. Specific examples thereof are an amino group (an amino group having 0 to 20 or, preferably, 0 to 10 carbon(s) such as amino, methylamino, dimethylamino, diethylamino and dibenzylamino), an alkoxy group (an alkoxy group having 1 to 20 or, preferably, 1 to 10 carbon(s) such as methoxy, ethoxy and butoxy), an aryloxy group (an aryloxy group having 6 to 20 or, preferably, 6 to 15 carbons such as phenyloxy and 2-naphthyloxy), a heterocyclic oxy group (a heterocyclic oxy group having 1 to 20 or, preferably, 1 to 10 carbon(s) such as pyrrolidinyloxy, pyrimidinyloxy, pyridazinyloxy and benzimidazolyloxy), a silyloxy group (a silyloxy group having 3 to 20 or, preferably, 3 to 10 carbons such as trimethylsilyloxy and tert-butylsilyloxy), an acyl group (an acyl group having 1 to 20 or, preferably, 1 to 10 carbon(s) such as acetyl, benzoyl, formyl and pivaloyl), an alkoxycarbonyl group (an alkoxycarbonyl group having 2 to 20 or, preferably, 2 to 10 carbons such as methoxycarbonyl and ethoxycarbonyl), an aryloxycarbonyl group (an aryloxycarbonyl group having 6 to 20 or, preferably, 6 to 15 carbons such as phenyloxycarbonyl), an acyloxy group (an acyloxy group having 1 to 20 or, preferably, 1 to 10 carbon(s) such as such as acetoxy and benzoyloxy), an acylamino group (an acylamino group having 1 to 20 or, preferably, 1 to 10 carbon(s) such as acetylamino and benzoylamino), an alkoxycarbonylamino group (an alkoxycarbonyl amino group having 2 to 20 or, preferably, 2 to 10 carbons such as methoxycarbonylamino), an aryloxycarbonylamino group (an aryloxycarbonylamino group having 6 to 20 or, preferably, 6 to 15 carbons such as phenyloxycarbonylamino), an alkyl or arylsulfonylamino group (an alkyl or arylsulfonylamino group having 1 to 20 or, preferably, 1 to 10 carbon(s) such as such as methanesulfonylamino and benzenesulfonylamino), a sulfamoyl group (a sulfamoyl group having 0 to 20 or, preferably, 0 to 10 carbon(s) such as sulfamoyl, N-methylsulfamoyl, N,N-dimethylsulfamoyl and N-phenylsulfamoyl), a carbamoyl group (a carbamoyl group having 1 to 20 or, preferably, 1 to 10 carbon(s) such as carbamoyl, N-methylcarbamoyl, N,N-diethylcarbamoyl and N-phenylcarbamoyl), a ureido group (a ureido group having 1 to 20 or, preferably, 1 to 10 carbon(s) such as ureido, methylureido and phenylureido), hydroxyl group, halogen atom (such as fluorine atom, chlorine atom, bromine atom and iodine atom), cyano group, sulfo group, imino group and heterocyclic group.

Such a substituent may be directly connected to a norbornene ring, may be connected via an alkylene group or the like or may be further substituted. When there are two or more substituents, they may be same or different. In case it is possible, they may be connected each other to form a ring. With regard to the polar group, preferred ones are an amino group, an alkoxy group, an aryloxy group, a heterocyclic oxy group, a silyloxy group, an acyl group, an alkoxycarbonyl group, an aryloxycarbonyl group, an acyloxy group, an acylamino group, an alkoxycarbonylamino group and an aryloxycarbonylamino group and more preferred ones are an alkoxycarbonyl group, an acyloxy group, an acylamino group and an alkoxycarbonylamino group.

Specific examples of the norbornene compound represented by the formula (B) are the following compounds although the present invention is not limited thereto.

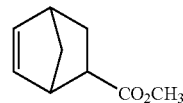

M-II-1

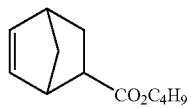

M-II-2

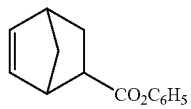

M-II-3

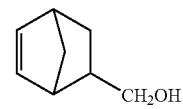

M-II-4

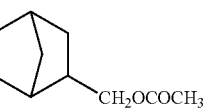

M-II-5

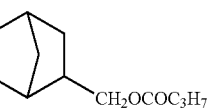

M-II-6

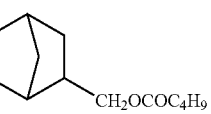

M-II-7

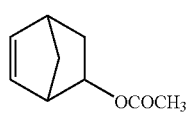

M-II-8

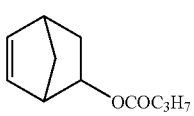

M-II-9

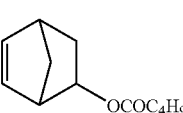

M-II-10

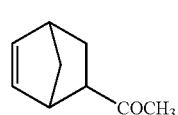

M-II-11

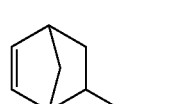

M-II-12

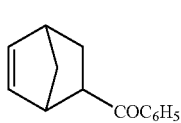

M-II-13

-continued

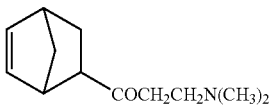
M-II-14

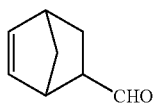
M-II-15

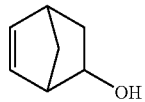
M-II-16

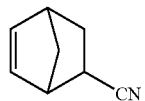
M-II-17

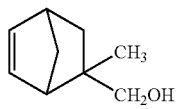
M-II-18

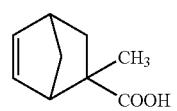
M-II-19

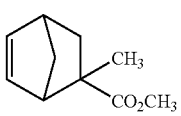
M-II-20

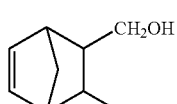
M-II-21

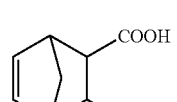
M-II-22

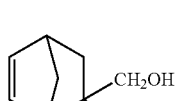
M-II-23

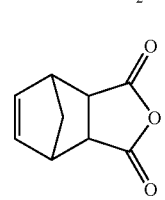
M-II-24

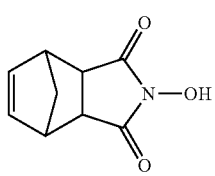
M-II-25

-continued

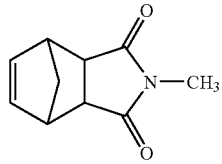
M-II-26

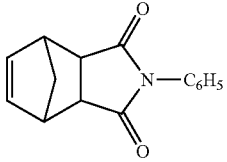
M-II-27

The norbornene compound represented by the formula (B) is able to be synthesized by conventional methods and, for example, it is able to be synthesized by the reaction of cyclopentadiene or dicyclopentadiene with the corresponding olefin.

(Organometallic Complex Catalyst)

In the process for production of polymers of the norbornene compound according to the present invention, the polymerization reaction is carried out by producing an organometallic complex catalyst by mixing the following compounds (a) and (d). The compound (a), the compound (d) and the organometallic complex catalyst will be illustrated as hereunder.

(a) Neutral Organopalladium Complex

The compound (a) which is used as a main catalyst in the process for production of polymers of norbornene compound according to the present invention is a neutral organopalladium complex having (i) palladium and (ii) two organic ligands where carbon atoms participating in the bond to palladium are at least three whereby it is neutral. At that time, both of the two organic ligands are preferred to be univalent carboanions and palladium is preferred to be a divalent palladium. When the two organic ligands are univalent carboanions and palladium is a divalent palladium, charge of the organopalladium complex as a whole is 0 whereby it is neutral. The two organic ligands are coordinately bonded to palladium and, in both of the two organic ligands, at least three carbon atoms are participated in the coordination bond.

The neutral organopalladium complex used in the present invention relating to the means for solving the second object is the same as in the present invention relating to the means for solving the first object. Further, the neutral organopalladium complex is preferably represented by the formulae (I) to (IV) described above, and the definitions of the symbols in the formulae (I) to (IV) are also the same. Specific examples of the palladium complex are exemplified above as Compounds 1 to 29 although they are non-limitative.

(d) Trisubstituted Ammonium tetrakis(aryl) Borate

A trisubstituted ammonium tetrakis(aryl) borate which is used as an auxiliary catalyst in a production process for the polymers of a norbornene compound according to the present invention is a salt comprising a trisubstituted ammonium as cation and a tetrakis(aryl) borate as anion.

When the compound (d) is mixed with the compound (a), proton of the trisubstituted ammonium conducts an electrophilic attack to anionic organic ligand of the compound (a) and the anionic organic ligand is detached as hydrocarbon. As a result thereof, neutral trisubstituted amine (i), organometallic complex catalyst (ii) and tetrakis(aryl) borate (iii) which is a counter-anion thereof are generated. Since the detached hydrocarbon has a sufficiently high pK$_a$, it does not react with the generated trisubstituted amine and, therefore, no reverse reaction proceeds. The organometallic complex catalyst (ii) is able to activate the polymerization reaction of the norbornene compound and, to be specific, it is thought to become a complex such as a cationic allyl palladium complex.

When production of the organometallic catalyst as such is carried out in a reaction system where compound of norbornene is polymerized, the organometallic complex catalyst is able to be produced efficiently in the polymerization system by the above-mentioned catalyst producing mechanism. Accordingly, it is possible to repeat the coordination and the insertion of the norbornene compound to and into the organometallic complex catalyst in situ whereby the polymerization is able to be made to proceed quickly.

The trisubstituted ammonium used for the process for production of the polymers of norbornene compound according to the present invention is a substance where three hydrogen atoms of ammonium ion are substituted with alkyl and/or aryl group(s) and is able to be represented by the following formula (V).

Formula (V)

In the formula, R$_A$, R$_B$ and R$_C$ each is an alkyl group or an aryl group being same or different and may be bonded each other to form a ring structure.

In the production mechanism of the above-mentioned organometallic complex catalyst, there may the cases where, if the trisubstituted amine generated from the trisubstituted ammonium has no steric bulkiness of some extent, it is re-coordinated to palladium atom in the organometallic complex catalyst to lower the activity of the polymerization reaction. Therefore, it is preferred that the trisubstituted ammonium is bulky to such an extent that it is not re-coordinated to palladium atom or has a steric hindrance of some extent.

With regard to a substituent for trisubstituted ammonium, carbon numbers are preferably 1 to 18, more preferably 1 to 6 and, still more preferably, 1 to 3 for an alkyl group while, for an aryl group, carbon numbers are preferably 6 to 18 and, more preferably, 6 to 12. With regard to a combination thereof, the case where at least one is an aryl group is preferred and the case of dialkyl aryl ammonium is more preferred.

Tetrakis(aryl) borate is a compound where four aryl groups are bonded to central boron and is represented by the following formula (VI).

Formula (VI)

In the formula, R$_D$, R$_E$, R$_F$ and R$_G$ each is an aryl group which may be same or different and may be bonded each other to form a ring structure.

In the tetrakis(aryl) borate; boron has no unshared electron pair and, in addition, it is surrounded by four bulky aryl groups whereby it is not coordinated to a cationic palladium complex. As a result, the cationic palladium complex functions as a catalytically active species.

In order to further improve the function, it is preferred to increase the cationic charge density of the cationic palladium complex. For such a purpose, it is preferred to improve the anionic charge density of the tetrakis(aryl) borate. A specific example therefor is to introduce an electron-attractive group into the aryl group. For example, introduction of fluorine is preferred.

Examples of the tetrakis(aryl) borate as such are tetrakis (phenyl) borate, tetrakis(pentafluorophenyl) borate, tetrakis (3,5-bis(trifluoromethyl)phenyl) borate, tetrakis(2-fluorophenyl) borate, tetrakis(3-fluorophenyl) borate, tetrakis(4-fluorophenyl) borate, tetrakis(4,5-difluorophenyl) borate, tetrakis(2,3,4,5-tetrafluorophenyl) borate, tetrakis(3,4,5,6-tetrafluorophenyl) borate, tetrakis(3,4,5-trifluorophenyl) borate, phenyl tris(perfluorophenyl) borate, tetrakis(4-tri-isopropylsilyltetrafluorophenyl) borate, tetrakis(4-dimethyl-tert-butylsilyltetrafluorophenyl) borate, tetrakis[3,5-bis[1-methoxy-2,2,2-trifluoro-1-(trifluoromethyl)ethyl]phenyl) borate, tetrakis([2-[1-methoxy-2,2,2-trifluoro-1-(trifluoromethyl)-ethyl]-5-(trifluoromethyl)phenyl] borate and tetrakis [3-[2,2,2-trifluoro-1-(2,2,2-trifluoroethoxy)-1-(trifluoromethyl)ethyl]-5-(trifluoromethyl)phenyl] borate although they are non-limitative.

Among them, preferred ones are tetrakis(pentafluorophenyl) borate, tetrakis(3,5-bis(trifluoromethyl)phenyl) borate, tetrakis(2-fluorophenyl) borate, tetrakis(3-fluorophenyl) borate, tetrakis(4-fluorophenyl) borate, tetrakis(4,5-difluorophenyl) borate, tetrakis(2,3,4,5-tetrafluorophenyl) borate, tetrakis(3,4,5,6-tetrafluorophenyl) borate, tetrakis(3,4,5-trifluorophenyl) borate, phenyl tris(perfluorophenyl) borate, tetrakis(4-tri-isopropylsilyltetrafluorophenyl) borate, tetrakis (4-dimethyl-tert-butylsilyltetrafluorophenyl) borate, tetrakis [3,5-bis[1-methoxy-2,2,2-trifluoro-1-(trifluoromethyl) ethyl]phenyl) borate, tetrakis([2-[1-methoxy-2,2,2-trifluoro-1-(trifluoromethyl)-ethyl]-5-(trifluoromethyl)phenyl] borate and tetrakis[3-[2,2,2-trifluoro-1-(2,2,2-trifluoroethoxy)-1-(trifluoromethyl)ethyl]-5-(trifluoromethyl)phenyl] borate having high anionic charge density, more preferred ones are tetrakis(pentafluorophenyl) borate and tetrakis(3,5-bis(trifluoromethyl)phenyl) borate and the particularly preferred one is tetrakis(pentafluorophenyl) borate.

As a result of a combination of the trisubstituted ammonium with tetrakis(aryl) borate as mentioned above, the compound (d) used for the production process of the present invention is able to be prepared. To be more specific, preferred ones are 2,6-dimethylanilinium tetrakis(3,5-difluorophenyl) borate, N,N-dimethylanilinium tetrakis(pentafluorophenyl) borate and N,N-dimethylanilinium tetrakis[3,5-bis(trifluoromethyl)-phenyl] borate and more preferred one is N,N-dimethylanilinium tetrakis(pentafluorophenyl) borate.

(Catalyst for Polymerization of a Norbornene Compound)

In the process for production of the polymers of a norbornene compound according to the present invention, the above-mentioned compounds (a) and (d) are mixed to produce an organometallic complex catalyst and the norbornene compound is polymerized. The compounds (a) and (d) react to give a catalytically active species which is a cationic palladium complex and charge of this cationic complex is univalent or divalent. Therefore, amount of the compound (d) to the compound (a) is preferably 0.1 to 10 equivalent(s), more preferably 0.5 to 5 equivalent(s) and, particularly preferably, 1 to 5 equivalent(s).

In the process for production of the polymer of a norbornene according to the present invention, the compounds (a) and (d) are mixed and the resulting uniform solution is used as a catalytically active species. When the norbornene compound is liquid and is able to dissolve the compounds (a) and (d), the compounds may also be directly added to the norbornene compound followed by mixing.

On the other hand, when the compounds (a) and (d) are dissolved in a solvent and then mixed, there may be some cases where the solvent is coordinated to palladium and lowers the activity of the catalyst. Therefore, the solvent is preferred to be nonpolar or lowly polar and the compounds may be dissolved in toluene for example. Since the compound (d) is a salt, it may be sometimes insoluble in nonpolar or lowly polar solvent and, in that case, it may be used after dissolving in a lowly polar solvent of a halogen type such as methylene chloride.

In the process for production of polymer of a norbornene compound according to the present invention, yellowish color of the polymer becomes deep when amount of the catalyst is high while, when the amount is low, the reaction becomes time-consuming or the yield decreases. Therefore, amount of the compound (a) is adjusted so as to make amount of palladium to 1 equivalent of the monomer of the norbornene compound preferably 1/10,000,000 to 1/1,000 equivalent, more preferably 1/1,000,000 to 1/1,000 equivalent and, most preferably, 1/1,000,000 to 1/2,000 equivalent.

In the process for production of polymers of a norbornene compound according to the present invention, there may be some cases where catalytic activity lowers by contamination of air, water, impurities in the norbornene compound, etc. Therefore, it is preferred that the norbornene compound used for polymerization is purified by distillation or recrystallization before use. Purity of the norbornene compound is preferably 95 to 100%, more preferably 98 to 100% and, particularly preferably, 99 to 100%.

(Control of Copolymerization Reaction)

When two or more norbornene compounds for polymerization are used and when their polymerization rates are greatly different, there may be the case where molecular weight distribution which is {[weight-average molecular weight (Mw)]/[number-average molecular weight (Mn)]} becomes 4 or more whereby that is not appropriate for film. In that case, the molecular weight distribution is able to be made small by addition of a norbornene compound having a high polymerization rate during the progress of the polymerization reaction.

(Adjusting Agent for Molecular Weight)

In the process for production of polymers of a norbornene compound according to the present invention, an aimed polymer is produced by vinyl polymerization of double bond in the norbornene compound. The norbornene compound represented by the formula (I) has a high polymerizing property and, therefore, there may be the case where molecular weight becomes too high whereby some components being insoluble in the solvent may be produced. In that case, the molecular weight is able to be lowered if an α-olefin is made to coexist.

With regard to the molecular weight of the polymers of a norbornene compound prepared by the production process of the present invention, it is preferred to be 10,000 to 10,000,000, more preferably 10,000 to 1,000,000 and, particularly preferably, 30,000 to 1,000,000. (In the present invention, a molecular weight stands for a number-average molecular weight unless otherwise mentioned.)

(Copolymerization with Other Component)

In the process for production of polymers of a norbornene compound according to the present invention; it is also possible to copolymerize with olefin or carbon monoxide other than the norbornene compound. In the case of olefin, that where no β-hydrogen detachment takes place is used while, in the case of carbon monoxide, it is possible to copolymerize by formation of an alternating copolymerization with a norbornene compound.

(Environment for Polymerization Reaction)

In the process for production of polymers of a norbornene compound according to the present invention, catalyst may be inactivated by the presence of air or water whereupon polymerizing property lowers or no polymerization proceeds. Accordingly, it is preferred to be operated in an atmosphere of highly pure inert gas.

(Solvents for Polymerization Reaction)

When the norbornene compound is liquid and is able to dissolve (a) and (d), it is also possible that they are mixed without solvent and made to react neatly as mentioned already. However, as the reaction proceeds, viscosity increases and stirring may become difficult and, therefore, it is desirable to use a solvent whereby the norbornene compound is dissolved. With regard to a solvent which dissolves the norbornene compound, that which does not lower the activity of the organometallic catalyst produced as a catalyst is preferred and a lowly polar solvent which is hardly coordinated to the catalyst is more preferred. Further, a solvent which is able to dissolve the resulting polymer is preferred. Examples of such a solvent are aromatic hydrocarbons such as benzene, toluene, xylene, cumene, p-cymene and mesitylene and, among them, preferred ones are toluene and xylene and still more preferred one is toluene.

On the other hand, when polarity of the solvent is too low, there may be the cases where the norbornene compound or the polymer of a norbornene compound is unable to be dissolved. Therefore, it is necessary to use an appropriate solvent depending upon the norbornene compound used therefor or a mixed solvent may be prepared by addition of an appropriate polar solvent to the abovementioned lowly polar solvent. Examples of such a polar solvent are methylene chloride and dichloroethane.

Amount of the solvent used in polymerization of the norbornene compound (in the case of addition and mixing after the compounds (a) and (d) are dissolved, the amount includes the amount of the solvent) to the norbornene compound is preferably 0 to 50 part(s) by mass, more preferably 0.3 to 20 part(s) by mass and, still more preferably, 0.5 to 5 part(s) by mass.

When the solvent is contaminated with air or water, the catalyst is inactivated and the polymerizing property may lower or the polymerization may not proceed. Therefore, when a solvent is used, the solvent is preferred to be subjected to dehydrating distillation and deaeration before use.

(Temperature for Polymerization Reaction)

Although the polymerization reaction of the present invention proceeds even at the temperature which is lower than room temperature, the reaction is able to be accelerated by heating. However, too much heating causes decomposition of the catalytically active species. Therefore, temperature for the reaction is preferably from room temperature to 150° C., more preferably 50 to 130° C. and, most preferably, 70 to 120° C.

(Reaction Time for Polymerization Reaction)

In the process for production of polymers of a norbornene compound according to the present invention, although reaction time of the polymerization reaction of the present invention is dependent upon reaction temperature, amount of the solvent, type of the polar group-containing norbornene, etc., the reaction is able to be finished within several tens minutes to ten-odd hours. Finish of the reaction is able to be judged by generation of palladium black in the reaction solution and, since the reaction time may become long, it is desired to finish appropriately.

(After-Treatment of Polymerization Reaction)

After stopping the heating of the reaction solution, the reaction as it is or after diluting with an appropriate solvent is mixed with a poor solvent (such as a solvent of an alcohol type, e.g. methanol) whereupon a solid in white to yellowish white color is obtained. This is filtered and dried in vacuo to give a polar group-containing norbornene polymer. When an appropriate reducing agent is used, residual divalent palladium is able to be made into palladium black and, when it is removed by filtration, a white polymer wherefrom yellowish color is further removed is able to be prepared.

EXAMPLES

The present invention relating to the means for solving the first object will now be illustrated by way of the following Examples of the present invention and Comparative Examples although the present invention is not limited thereto.

Example 1-1

Methyl norbornene carboxylate M-1 (ratio of endo/exo=51/49; manufactured by Tokyo Kasei) (20.0 g) as a monomer and 40 mL of toluene were charged in a glass container where inner air was substituted with highly pure argon and were stirred with a stirring fan. A solution where 13.6 mg of an organopalladium complex as (a) was dissolved in 0.5 mL of toluene, a solution where 4.9 mg of triphenyl phosphine $P(C_6H_5)_3$ (manufactured by Wako Pure Chemical Industry) (4.9 mg) as (b) was dissolved in 0.5 mL of toluene and a solution where dimethylanilinium tetrakispentafluoro borate $(CH_3)_2(H)NC_6H_5.B(C_6F_5)_4$ (manufactured by Strem) (54 mg) as (c) was dissolved in 1 mL of methylene chloride were added thereto. The mixed solution was heated until the inner temperature became 90° C. and the reaction was carried out for 6 hours by keeping the temperature at 90° C. After completion of the reaction, the reaction solution was added to 300 mL of methanol. The resulting white solid was sucked and dried in vacuo at 100° C. for 6 hours to give 14.8 g of white solid.

Number-average molecular weight (Mn) and weight-average molecular weight (Mw) of the resulting polymer were measured as the values for polystyrene by a gel permeation chromatography (GPC) where tetrahydrofuran was used as a solvent.

Examples 1-2 to 1-9

The same experiment as in Example 1-1 was carried out where the neutral organopalladium complex (a), the organophosphorus compound (b), the salt (c) and the monomer were changed as shown in the following Table 1. Molar equivalents in each Example were the same as those in Example 1-1.

Example 1-10

The same experiment as in Example 1-1 was carried out except that the monomer was changed to M-1 and norbornene (NB) in a molar ratio of 70/30.

Comparative Examples 1-1 to 1-2

The same experiment as in Example 1-1 was carried out where the neutral organopalladium complex (a), the organophosphorus compound (b), the salt (c) and the monomer were changed as shown in the following Table 1. Molar equivalents in each Example were the same as those in Example 1-1. Although reprecipitation was conducted in Comparative Example 1-1, no solid was produced. In Comparative Example 1-2, yield of the separated solid was little and no analysis such as molecular weight was conducted.

TABLE 1

| | (a) | (b) | (c) | Monomer | Yield | Mw | Mn |
|---|---|---|---|---|---|---|---|
| Example 1-1 | 1 | $P(C_6H_5)_3$ | $(CH_3)_2(H)NC_6H_5 \cdot B(C_6F_5)_4$ | M-1 | 74% | 33800 | 104700 |
| Example 1-2 | 1 | $P(C_6H_{11})_3$ | $(CH_3)_2(H)NC_6H_5 \cdot B(C_6F_5)_4$ | M-1 | 81% | 31000 | 100300 |
| Example 1-3 | 1 | $P(C_6H_5)_3$ | $(CH_3)_2(H)NC_6H_5 \cdot B(C_6F_5)_4$ | M-2 | 65% | 34400 | 102300 |
| Example 1-4 | 1 | $P(C_6H_5)_3$ | $(CH_3)_2(H)NC_6H_5 \cdot B(C_6F_5)_4$ | M-5 | 56% | 30300 | 96000 |
| Example 1-5 | 2 | $P(C_6H_5)_3$ | $(CH_3)_2(H)NC_6H_5 \cdot B(C_6F_5)_4$ | M-1 | 77% | 31000 | 99300 |
| Example 1-6 | 3 | $P(C_6H_5)_3$ | $(CH_3)_2(H)NC_6H_5 \cdot B(C_6F_5)_4$ | M-1 | 81% | 35300 | 102000 |
| Example 1-7 | 4 | $P(C_6H_5)_3$ | $(CH_3)_2(H)NC_6H_5 \cdot B(C_6F_5)_4$ | M-1 | 77% | 37500 | 112300 |
| Example 1-8 | 5 | $P(C_6H_5)_3$ | $(CH_3)_2(H)NC_6H_5 \cdot B(C_6F_5)_4$ | M-1 | 73% | 39000 | 121100 |
| Example 1-9 | 6 | $P(C_6H_5)_3$ | $(CH_3)_2(H)NC_6H_5 \cdot B(C_6F_5)_4$ | M-1 | 68% | 31500 | 112000 |
| Example 1-10 | 1 | $P(C_6H_5)_3$ | $(CH_3)_2(H)NC_6H_5 \cdot B(C_6F_5)_4$ | M-1/NB | 72% | 14400 | 98800 |
| Comparative Example 1-1 | 1 | (none) | $(CH_3)_2(H)NC_6H_5 \cdot B(C_6F_5)_4$ | M-1 | — | — | — |
| Comparative Example 1-2 | 1 | (none) | $(C_6H_5)_3C \cdot B(C_6F_5)_4$ | M-1 | <30% | — | — |

As will be apparent from the above table, the catalytic system of the present invention shows an excellent catalytic activity for polymerization to any polar group-containing norbornene.

The present invention relating to the means for solving the second object will now be illustrated by way of the following Examples of the present invention and Comparative Examples although the present invention is not limited thereto.

Synthetic Examples

Synthesis of the Compound M-I-11

Dicyclopentadiene (manufactured by Wako Pure Chemical Industry) (158.2 g), 313.3 g of 1-octene (manufactured by Wako Pure Chemical Industry) and 2.5 g of Irganox 1010 (manufactured by Ciba Specialty Chemicals) were charged in a one-liter autoclave and the space was substituted with nitrogen. In a tightly closed system, stirring was conducted for 4 hours where inner temperature was 200° C. (revolving rate=300 rpm). The reaction mixture was filtered and the volatile component was evaporated. The residue was subjected to a precise distillation (theoretical plate numbers=five; ratio of opening/closing time of refluxing=5/1; pressure=7 mmHg; top temperature=89 to 90° C.) to give 111.0 g of colorless and transparent liquid. The resulting colorless and transparent liquid was subjected to a gas chromatography and its peak purity was measured whereupon it was a norbornene compound where purity was not lower than 99% and an endo/exo ratio was 79/21.

Synthesis of the compound M-II-1

Dicyclopentadiene (manufactured by Wako Pure Chemical Industry) (264.4 g), 516.5 g of methyl acrylate (manufactured by Wako Pure Chemical Industry) and 5.0 g of Irganox 1010 (manufactured by Ciba Specialty Chemicals) were charged in a two-liter autoclave and the space was substituted with nitrogen. In a tightly closed system, stirring was conducted for 4 hours where inner temperature was 200° C. (revolving rate=300 rpm). The volatile component was evaporated. The residue was subjected to a precise distillation (theoretical plate numbers=40; ratio of opening/closing time of refluxing=30/1 to 1/1; pressure=12 mmHg; top temperature=80 to 82° C.) to give 482.2 g of colorless and transparent liquid. The resulting colorless and transparent liquid was subjected to a gas chromatography and its peak purity was measured whereupon it was a norbornene compound where purity was not lower than 99% and an endo/exo ratio was 49/51.

(Synthesis of Palladium Complexes 1 to 6)

The palladium complexes 1 to 6 are synthesized by the same ways as explained above.

(Measurement of Molecular Weight)

Weight-average molecular weight (Mw) and number-average molecular weight (Mn) of the samples prepared in Examples and Comparative Examples were measured as the values for polystyrene by a gel permeation chromatography (GPC) where tetrahydrofuran was used as a solvent.

(Measurement of Yellowishness)

The polymers prepared in Examples and Comparative Examples were judged by naked eye whether yellowish color was noted.

Example 2-1

M-I-1 (manufactured by Aldrich) (24.6 g) as a norbornene compound and 50 mL of toluene were charged in a glass container where inner air was substituted with highly pure argon and were stirred with a stirring fan. A solution where 13.6 mg of an organopalladium complex 1 as (a) (refer to the above-mentioned synthetic example for its synthetic method) was dissolved in 0.5 mL of toluene and a solution where N,N-dimethylanilinium tetrakis(pentafluorophenyl) borate $(CH_3)_2(H)NC_6H_5 \cdot B(C_6F_5)_4$ (manufactured by Strem) (54 mg) as (b) was dissolved in 1 mL of methylene chloride were added thereto. When the mixed solution was heated, it solidified in white at about 50° C. and stirring was not possible. As such, white solid of the polymer of a norbornene compound was prepared. Since the resulting white solid was insoluble in a solvent, molecular weight analysis, etc. were not conducted. Result of measurement of the yellowishness was shown in Table 2.

Example 2-2

M-I-11 (15.7 g) as a norbornene compound, 4.2 g of 1-octene (manufactured by Wako Pure Chemical Industry) as a molecular weight adjusting agent and 40 mL of toluene were charged in a glass container where inner air was substituted with highly pure argon and were stirred with a stirring fan. A solution where 0.6 mg of the organopalladium complex 1 (refer to the above-mentioned synthetic example for its synthesis) as the compound (a) dissolved in 0.5 mL of toluene and a solution where 8 mg of N,N-dimethylanilinium tetrakis (pentafluorophenyl) borate $(CH_3)_2(H)NC_6H_5 \cdot B(C_6F_5)_4$ (manufactured by Strem) as the compound (d) was dissolved in 0.5 mL of methylene chloride were added thereto. The mixed solution was heated until the inner temperature became 90° C. and the reaction was carried out for 3 hours by keeping the temperature at 90° C. After completion of the reaction, the reaction solution was diluted with 200 mL of toluene and added to 300 mL of methanol. The resulting white solid was sucked and dried in vacuo at 100° C. for 6 hours. As such, 14.7 g of white solid of the polymer of a norbornene compound was prepared. Result of measurement of yellowishness, measurement of molecular weight and measurement of yield were shown in Table 2.

Examples 2-3 to 2-7

Polymers of a norbornene compound were prepared by the same manner as in Example 2-2 except that a neutral organopalladium complex which is a compound (a), a compound (d) and a norbornene compound which is a starting material were changed as shown in the following Table 2. Result of measurement of yellowishness, measurement of molecular weight and measurement of yield were shown in Table 2.

Example 2-8

Polymer of a norbornene compound was prepared by the same manner as in Example 2-2 except that a norbornene compound used as a starting material was changed to M-I-1 (manufactured by Aldrich) and M-II-1 (refer to the above synthetic examples for its synthetic method) where their molar ratio was made 90/10. Result of measurement of yellowishness, measurement of molecular weight and measurement of yield were shown in Table 2.

Comparative Examples 2-1 to 2-3

Polymerization of a norbornene compound was carried out by the same manner as in Example 2-1 except that the compound (a), the compound (d) and the norbornene compound used as the starting material were changed as shown in the following Table 2. In Comparative Example 2-3, its copolymerizing ratio was made the same as that in Example 2-8. Result of measurement of yellowishness, measurement of molecular weight and measurement of yield were shown in Table 2.

The product prepared in Comparative Example 2-1 solidified in a flask and a part of the content was unable to be taken out. Therefore, its yield was not calculated. Further, since the polymer was insoluble in a solvent, molecular weight analysis was not conducted.

TABLE 2

| | Norbornene compound | Compound (a) | Compound (d) | Yield | Mw | Mn | Yellowish-ness |
|---|---|---|---|---|---|---|---|
| Example 2-1 | M-I-1 | 1 | $(CH_3)_2(H)NC_6H_5 \cdot B(C_6F_5)_4$ | — | — | — | not noted |
| Example 2-2 | M-I-11 | 2 | $(CH_3)_2(H)NC_6H_5 \cdot B(C_6F_5)_4$ | 94% | 252500 | 87400 | not noted |
| Example 2-3 | M-I-11 | 3 | $(CH_3)_2(H)NC_6H_5 \cdot B(C_6F_5)_4$ | 90% | 242000 | 90500 | not noted |
| Example 2-4 | M-I-11 | 4 | $(CH_3)_2(H)NC_6H_5 \cdot B(C_6F_5)_4$ | 88% | 264000 | 92000 | not noted |
| Example 2-5 | M-I-11 | 4 | $(CH_3)_2(H)NC_6H_5 \cdot B(C_6F_5)_4$ | 91% | 234000 | 88200 | not noted |
| Example 2-6 | M-I-11 | 5 | $(CH_3)_2(H)NC_6H_5 \cdot B(C_6F_5)_4$ | 95% | 223500 | 89300 | not noted |
| Example 2-7 | M-I-11 | 6 | $(CH_3)_2(H)NC_6H_5 \cdot B(C_6F_5)_4$ | 89% | 210400 | 92400 | not noted |
| Example 2-8 | M-I-1/M-II-1 | 1 | $(CH_3)_2(H)NC_6H_5 \cdot B(C_6F_5)_4$ | 65% | 154300 | 24500 | not noted |
| Comp Ex 2-1 | M-I-1 | 1 | $(CH_3)_3C \cdot B(C_6F_5)_4$ | — | — | — | noted |
| Comp Ex 2-2 | M-I-11 | 1 | $(CH_3)_3C \cdot B(C_6F_5)_4$ | 85% | 193400 | 72000 | noted |
| Comp Ex 2-3 | M-I-1/M-II-1 | 1 | $(CH_3)_3C \cdot B(C_6F_5)_4$ | 57% | 142300 | 190200 | noted |

As will be apparent from the above table, polymers where yellowishness was suppressed was able to be prepared in a good yield in accordance with the process for production of polymers of a norbornene compound according to the present invention.

INDUSTRIAL APPLICABILITY

In accordance with the present invention, it is now possible to produce a polymer of polar group-containing norbornene of a broad range by an industrially advantageous amount of a catalyst. It is also possible to produce a polar group-containing norbornene polymer having little coloration and being useful as optical materials, etc.

Further, in accordance with the production process of the present invention, polymers of a norbornene compound having high heat resistance, low double refraction, stability to moisture and little degree of coloration and being able to give an excellent film having high transparency are able to be produced in a high yield.

The entire disclosure of each and every foreign patent application from which the benefit of foreign priority has been claimed in the present application is incorporated herein by reference, as if fully set forth.

The invention claimed is:

1. An organometallic compound obtained by mixing following (a), (b) and (c):
   (a) a neutral organopalladium complex that has a palladium atom and two organic ligands each having at least three carbon atoms participating in a bond to the palladium atom;
   (b) an organophosphorus compound having one phosphorus atom; and
   (c) a salt comprising: an anion having no unshared electron pair in a central atom; and a counter-cation.

2. The organometallic compound according to claim 1, wherein one organic ligand of the two organic ligands has three carbon atoms participating in a bond to the palladium atom, and the other organic ligand of the two organic ligands has five carbon atoms participating in a bond to the palladium atom.

3. The organometallic compound according to claim 2, wherein the neutral organopalladium complex is represented by formula (I):

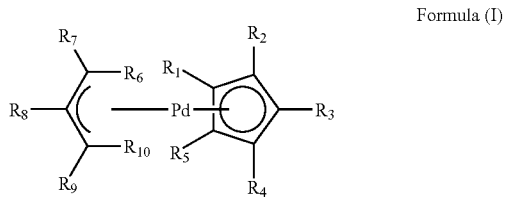

Formula (I)

wherein $R_1$, $R_2$, $R_3$, $R_4$, $R_5$, $R_6$, $R_7$, $R_8$, $R_9$ and $R_{10}$ each independently represents a hydrogen atom, a halogen atom or a univalent organic group, and may be bonded each other to form a ring structure.

4. The organometallic compound according to claim 2, wherein the neutral organopalladium complex is represented by formula (II):

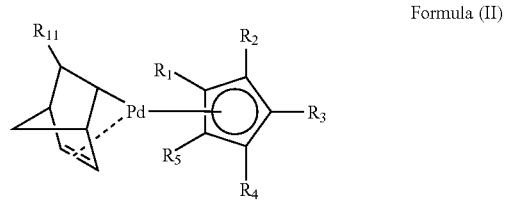

Formula (II)

wherein $R_1$, $R_2$, $R_3$, $R_4$, $R_5$ and $R_{11}$ each independently represents a hydrogen atom, a halogen atom or a univalent organic group, and may be bonded each other to form a ring structure; and a dotted line represents a coordination bond.

5. The organometallic compound according to claim 2, wherein the neutral organopalladium complex is represented by formula (III):

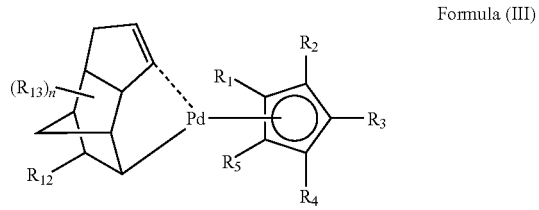

Formula (III)

wherein $R_1$, $R_2$, $R_3$, $R_4$, $R_5$, $R_{12}$ and $R_{13}$ each independently represents a hydrogen atom, a halogen atom or a univalent organic group, and may be bonded each other to form a ring structure;

n represents an integer of 1 to 12;
$(R_{13})_n$ represents substitutions of n number of $R_{13}$'s; and
a dotted line represents a coordination bond.

6. The organometallic compound according to claim 2, wherein the neutral organopalladium complex is represented by formula (IV):

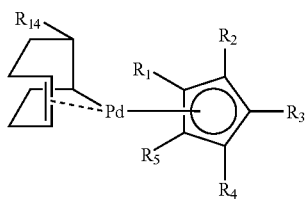

Formula (IV)

wherein $R_1$, R. $R_3$, $R_4$, $R_5$ and $R_{14}$ each independently represents a hydrogen atom, a halogen atom or a univalent organic group, and may be bonded each other to form a ring structure; and a dotted line represents a coordination bond.

7. A catalyst for polymerization of a polar group-containing norbornene, the catalyst is produced by utilizing an organometallic compound according to claim 1.

8. A process for producing a polar group-containing norbornene polymer, the process comprising:

polymerizing a polar group-containing norbornene by utilizing a catalyst for polymerization of a polar group-containing norbornene according to claim 7.

* * * * *